United States Patent
Xiong et al.

(10) Patent No.: US 7,141,390 B2
(45) Date of Patent: Nov. 28, 2006

(54) POLYNUCLEOTIDE ENCODING HUMAN INTERLEUKIN-17 RECEPTOR LIKE MOLECULE

(75) Inventors: Shiqin Xiong, Beijing (CN); Zhijie Chang, Beijing (CN); Fu Xinyuan, Beijing (CN)

(73) Assignee: Tsinghua University, Beijing (CN)

( * ) Notice: Subject to any disclaimer, the term of this patent is extended or adjusted under 35 U.S.C. 154(b) by 91 days.

(21) Appl. No.: 10/608,449

(22) Filed: Jun. 30, 2003

(65) Prior Publication Data

US 2004/0265834 A1 Dec. 30, 2004

(30) Foreign Application Priority Data

Jun. 28, 2003 (CN) ................................ 2123447 U

(51) Int. Cl.
*C12N 15/09* (2006.01)
*C12N 15/12* (2006.01)
*C12N 15/24* (2006.01)
*C07K 14/00* (2006.01)

(52) U.S. Cl. ................. 435/69.52; 435/69.1; 536/23.5; 530/351

(58) Field of Classification Search ............... 435/69.1, 435/320.1, 325, 471; 536/23.5; 530/350
See application file for complete search history.

(56) References Cited

OTHER PUBLICATIONS

Database GeneMBL. Accession No. AX08664; Mar. 9, 2001; Wiemann et al.*
Database GeneMBL. Accession No.; AL133097; Feb. 18, 2000, Bloecker et al.*
Database GeneMBL. Accession No.; AX251723; Oct. 5, 2001; S. Jing et al.*

* cited by examiner

*Primary Examiner*—Brenda Brumback
*Assistant Examiner*—Fozia Hamud
(74) *Attorney, Agent, or Firm*—Millen, White, Zelano, Branigan,P.C.

(57) ABSTRACT

The application relates to a newly identified polynucleotide, polypeptide encoded by such polynucleotide, the use of such polynucleotide and polypeptide, as well as the production of such polynucleotide and polypeptide. More particularly, the polypeptide of the present invention is human interleukin-17 receptor like molecule (IL-17RLM).

3 Claims, 25 Drawing Sheets

FIG. 1A

Figure 2A:
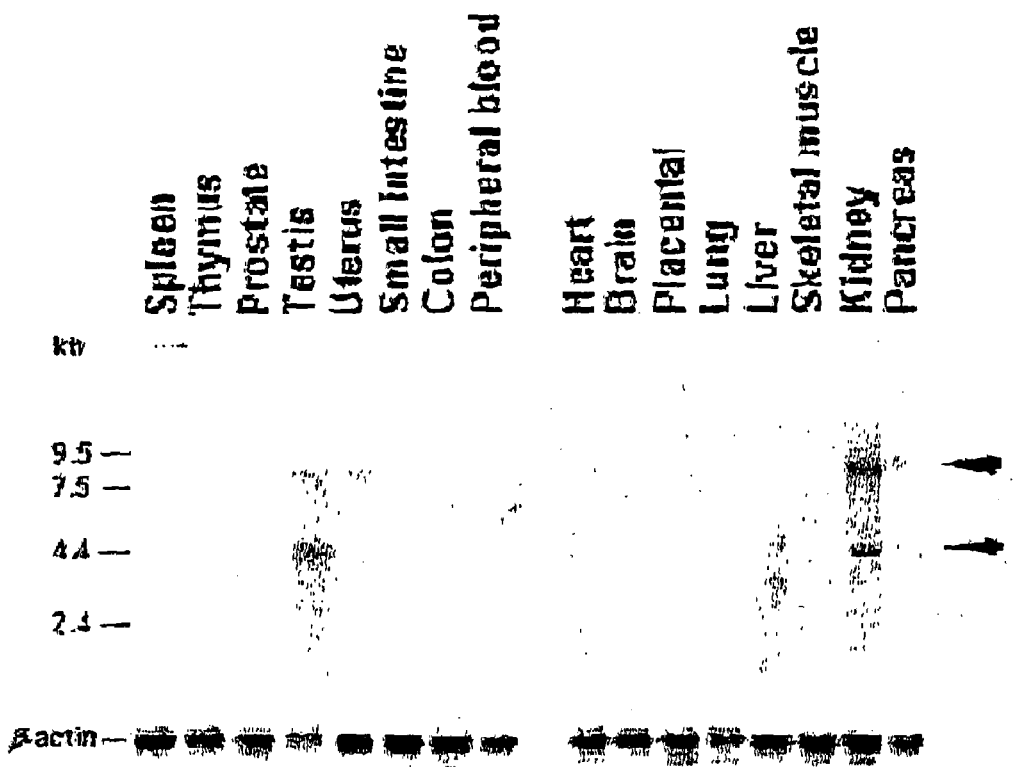

```
GCGGCCGCCGCGGCCACCGCCCACTCGGGGCTGGCCAGCGGCGGGCGGCCGGGGCGCAGAGAACGGCCTGGCTGGGCGAG
          M  A  P  W  L  Q  L  C  S  V  F  F  T  V  N  A  C  L  N  G  S  Q  L  A
CGCACGGCCATGGCCCCGTGGCTGCAGCTCTGCTCCGTCTTCTTTACGGTCAACGCCTGCCTCAACGGCTCGCAGCTGGC
  V  A  A  G  G  S  G  R  A  R  G  A  D  T  C  G  W  R  G  V  G  P  A  S  R  N
TGTGGCCGCTGGCGGGTCCGGCCGCGCGCGGGGCGCCGACACCTGTGGCTGGAGGGGAGTGGGGCCAGCCAGCAGAAACA
  S  G  L  Y  N  I  T  F  K  Y  D  N  C  T  T  Y  L  N  P  V  G  K  H  V  I  A  D
GTGGGCTGTACAACATCACCTTCAAATATGACAATTGTACCACCTACTTGAATCCAGTGGGGAAGCATGTGATTGCTGAC
  A  Q  N  I  T  I  S  Q  Y  A  C  H  D  Q  V  A  V  T  I  L  W  S  P  G  A  L  G
GCCCAGAATATCACCATCAGCCAGTATGCTTGCCATGACCAAGTGGCAGTCACCATTCTTTGGTCCCCAGGGGCCCTCGG
  I  E  F  L  K  G  F  R  V  I  L  E  E  L  K  S  E  G  R  Q  C  Q  Q  L  I  L
CATCGAATTCCTGAAAGGATTTCGGGTAATACTGGAGGAGCTGAAGTCGGAGGGAAGACAGTGCCAACAACTGATTCTAA
  K  D  P  K  Q  L  N  S  S  F  K  R  T  G  M  E  S  Q  P  F  L  N  M  K  F  E  T
AGGATCCGAAGCAGCTCAACAGTAGCTTCAAAAGAACTGGAATGGAATCTCAACCTTTCCTGAATATGAAATTTGAAACG
  D  Y  F  V  K  V  V  P  F  P  S  I  K  N  E  S  N  Y  H  P  F  F  F  R  T  R  A
GATTATTTCGTAAAGGTTGTCCCTTTTCCTTCCATTAAAAACGAAAGCAATTACCACCCTTTCTTCTTTAGAACCCGAGC
        C  D  L  L  L  Q  P  D  N  L  A  C  K  P  F  W  K  P  R  N  L  N  I  S  Q  H
CTGTGACCTGTTGTTACAGCCGGACAATCTAGCTTGTAAACCCTTCTGGAAGCCTCGGAACCTGAACATCAGCCAGCATG
  G  S  D  M  Q  V  S  F  D  H  A  P  H  N  F  G  R  F  F  Y  L  H  Y  K  L  K
GCTCGGACATGCAGGTGTCCTTCGACCACGCACCGCACAACTTCGGCTTCCGTTTCTTCTATCTTCACTACAAGCTCAAG
  H  E  G  P  F  K  R  K  T  C  E  Q  E  Q  T  T  E  M  T  S  C  L  L  Q  N  V  S
CACGAAGGACCTTTCAAGCGAAAGACCTGTGAGCAGGAGCAAACTACAGAGATGACCAGCTGCCTCCTTCAAAATGTTTC
  P  G  D  Y  I  I  E  L  V  D  D  T  N  T  T  R  K  V  M  H  Y  A  L  K  P  V
TCCAGGGGATTATATAATTGAGCTGGTGGATGACACTAACACAACAAGAAAAGTGATGCATTATGCCTTAAAGCCAGTGC
  H  S  P  W  A  G  P  I  R  A  V  A  I  T  V  P  L  V  V  I  S  A  F  A  T  L  F
ACTCCCCGTGGGCCGGGCCCATCAGAGCCGTGGCCATCACAGTGCCACTGGTAGTCATATCGGCATTCGCGACGCTCTTC
  T  V  M  C  R  K  K  Q  Q  E  N  I  Y  S  H  L  D  E  E  S  S  E  S  S  T  Y  T
ACTGTGATGTGCCGCAAGAAGCAACAAGAAAATATATATTCACATTTAGATGAAGAGAGCTCTGAGTCTTCCACATACAC
    A  A  L  P  R  E  R  L  R  P  R  P  K  V  F  L  C  Y  S  S  K  D  G  Q  N  H
TGCAGCACTCCCAAGAGAGAGGCTCCGGCCGCGGCCGGAAGGTCTTTCTCTGCTATTCCAGTAAAGATGGCCAGAATCACA
  M  N  V  V  Q  C  F  A  Y  F  L  Q  D  F  C  G  C  E  V  A  L  D  L  W  B  D  F
TGAATGTCGTCCAGTGTTTCGCCTACTTCCTCCAGGACTTCTGTGGCTGTGAGGTGGCTCTGGACCTGTGGGAAGACTTC
  S  L  C  R  E  G  Q  R  E  W  V  I  Q  K  I  H  E  S  Q  F  I  I  V  V  C  S  K
AGCCTCTGTAGAGAAGGGCAGAGAGAATGGGTCATCCAGAAGATCCACGAGTCCCAGTTCATCATTGTGGTTTGTTCCAA
  G  M  K  Y  F  V  D  K  K  N  Y  K  H  K  G  G  G  R  G  S  G  K  G  E  L  F
AGGTATGAAGTACTTTGTGGACAAGAAGAACTACAAACACAAAGGAGGTGGCCGAGGCTCGGGGAAAGGAGAGCTCTTCC
  L  V  A  V  S  A  I  A  E  K  L  R  Q  A  K  Q  S  S  S  A  A  L  S  K  F  I  A
TGGGTGGCGGTGTCAGCCATTGCCGAAAAGCTCCGCCAGGCCAAGCAGAGTTCGTCCGCGGCGCTCAGCAAGTTTATCGCC
  V  Y  F  D  Y  S  C  E  G  D  V  P  G  I  L  D  L  S  T  K  Y  R  L  M  D  N  L
GTCTACTTTGATTATTCCTGCGAGGGAGACGTCCCCGGTATCCTAGACCTGAGTACCAAGTACAGACTCATGGACAATCT
  P  Q  L  C  S  H  L  H  S  R  D  H  Q  E  P  G  Q  H  T  R  Q  G  S  R
TCCTCAGCTCTGTTCCCACCTGCACTCCCGAGACCACGGCCTCCAGGAGCCGGGCAGCACACGCGACAGGGCAGCAGAA
  R  N  Y  F  R  S  K  S  G  R  S  L  Y  V  A  I  C  N  M  H  Q  F  I  D  E  E  P
GGAACTACTTCCGGAGCAAGTCAGGCCGGTCCCTATACGTCGCCATTTGCAACATGCACCAGTTTATTGACGAGGAGCCC
  D  W  F  E  K  Q  F  V  P  F  H  P  P  P  L  R  Y  R  E  P  V  L  E  K  F  D  S
GACTGGTTCGAAAAGCAGTTCGTTCCCTTCCATCCTCCTCCACTGCGCTACCGGGAGCCAGTCTTGGAGAAATTTGATTC
  G  L  V  L  N  D  V  M  C  K  P  G  P  E  S  D  F  C  L  K  V  E  A  A  V  L
GGGCTTGGTTTTAAATGATGTCATGTGCAAACCAGGGCCTGAGAGTGACTTCTGCCTAAAGGTAGAGGCGGCTGTTCTTG
  G  A  T  G  P  A  D  S  Q  H  E  S  Q  H  G  G  L  D  Q  D  G  E  A  R  P  A  L
GGGCAACCGGACCAGCCGACTCCCAGCACGAGAGTCAGCATGGGGGCCTGGACCAAGACGGGGAGGCCCGGCCTGCCCTT
  D  G  S  A  A  L  Q  P  L  L  H  T  V  K  A  G  S  P  S  D  M  P  R  D  S  G  I
GACGGTAGCGCCGCCCTGCAACCCCTGCTGCACACGGTGAAAGCCGGCAGCCCCTCGGACATGCCGCGGGACTCAGGCAT
    Y  D  S  S  V  P  S  S  E  L  S  L  P  L  M  E  G  L  S  T  D  Q  T  E  T  S
CTATGACTCGTCTGTGCCCTCATCCGAGCTGTCTCTGCCACTGATGGAAGGACTCTCGACGGACCAGACAGAAACGTCTT
  S  L  T  E  S  V  S  S  S  G  L  G  E  E  E  P  P  A  L  P  S  K  L  L  S  S
CCCTGACGGAGAGCGTGTCCTCCTCTTCAGGCCTGGGTGAGGAGGAACCTCCTGCCCTTCCTTCCAAGCTCCTCTCTTCT
  G  S  C  K  A  D  L  G  C  R  S  Y  T  D  E  L  H  A  V  A  P  L  *
GGGTCATGCAAAGCAGATCTTGGTTGCCGCAGCTACACTGATGAACTCCACGCGGTCGCCCCTTTgTAAcAAAACGAAAC
AGTCTAAGCATTGCCACTTTAGCTGCTGCCTCCCTCTGATTCCCCAGCTCATCTCCCTGGTTGCATGGCCCACTTGGAGC
TGAGGTCTCATACAAGGATATTTGGAGTGAAATGCTGGCCAGTACTTGTTCTCCCTTGCCCCAACCCTTTACCGGATATC
TTGACAAACTCTCCAATTTTCTAAAATGATATGGAGCTCTGAAAGGCATGTCCATAAGGTCTGACAACAGCTTGCCAAAT
TTGGTTAGTCCTTGGATCAGAGCCTGTTGTGGGAGGTAGGGAGGAAATATGTAAAGAAAAACAGGAAGATACCTGCACTA
ATCATTCAGACTTCATTGAGCTCTGCAAACTTTGCCTGTTTGCTATTGGCTACCTTGATTTGAAATGCTTTGTGAAAAAA
GGCACTTTTAACATCATAGCCACAGAAATCAAGTGCCAGTCTATCTGGAATTCCATTGTATTGCAGATAATGTTCTCAT
TTATTTTTGATGTAGAATTTACATTGCCATGGGTGTTAAATAAGCTTTGAGTCAAAAGTCAAGAAAGTGACTGAATATAC
AGTCACCTTTTATGAAATGAGTCTCTGTGTTACTGGGTGGCATGACTGATTGAGGTGAAGCTCACGGGGCCAGGCTGACC
```

```
GTCTTGACCGTTCCACTTGAGATAGGTTGGTCATCGTGCAGAAGGCCCCAGGACCTCAGCACACACAGCCTCCTCTTGGT
CTGAGTAGGCATCATGTGGGGGCCAGATCTGCCTGCTGTTTCCATGGGTTACATTTACTGTGCTGTATCTCAGATGTTGG
TGTCTGGAAGTTTATTCTTAAGAGACTGCTACCCAGCTGGTCTGTATTATTGGAAGTTGCAGTTCGTGCTTTGGTTGGCC
TTCTGGTCTAAAGCTGTGTCCTGAATATTAGGGATCACAATTCACTGAAATACAGCAGTGTGTGGAGGTGATGGCCAGTT
AATCTGCTGAACTGGTTTTGACTAATGACAAACCTCTTTTTAAGATGGTAGAATGGAGGTGATAGTCACAAAAGTAAATG
TTCCATTTTTATGAATGACTTTCTACAGAGTTTCTATTTCTAAAGAAAAAAACAATTGTTCACATCCCATCTGATGATTAG
CATGTGTGTAATGAATGCTGTCTTGGTCTCCCCTGTGGAAACCCTTCTCCCTGTGCCTTAGAGCAGGTGTGTACATCTCT
CACTACCTTTCTCATGGGTGCTGTTAGATTTTGGCACCCGTTTTCTCAGCATTCAGCCCAGGGAATGTGGTTTTCACTTC
TTCGTCAGATAAGACCAACATGAAGGGGTATGTTGAGAAACATCCTGAGGCAAGGTGGGAGGTGGGATGGGGCAGGACTT
TCCCTTCCAAGCACATGCATGGCAGGTGGGGAAAGGGGGGCTTGCACCCCTGCTGGAAAGAAAAGGTTTGTGTATATTTC
TGATGCAAATGTCATACTCACTGCTCTGTAAAGGCAGCTGGCAGCTTTTTGGGAAAAGAACGTGCTCGTCTGTTCTCTGG
CATCAAGTTTCTTGCAGCTGCTCTGAGGGAGAGACAGTGAGCTGCAAGACTGCCTCCCCATAACAACAGGCAACTCAGAG
AAGAGTCATTTTATGTTGTTCCTATGGAATCTGGAATGAGTGCAGAGCTCCTACCCACACATGACTGCCCCGCCATTTCA
TCCTAGGCATTCTGTGAAGGAGATTGGTTAGTCCAAACTTGCTAACATACGAAAATTCACTTGGAACATGATGAGAGATT
TCTTATTGAGGCCAAGAGATGTTTCCTGTCCCAGAGGAACCATTAGGAGTCGCTTTTAGGGTATTCAGCTTTGTTCATGA
AATAAGGCATCTCTGAGAAAGTGGCCCCAGGGAGAGAATGGAGGACTGGGAGGAGAAGCATTAACTGAGCTCCAAGGGTG
TGTGGGCAGAGAGCTTGCTATGTGAACTCACTCCTTAAGAAAATGAAGAGAAAAAGAGAGTGCTAGTTAAAAAATCGGG
ATGTTTAGTTTGGATTTAGGGTTTTGATACTTATGTTGAAATACTAATGTTTCTGATCAATAAAATCAAACTCTTAATA
TACCGAGTAATGAAACCATAGTGTGATTGCCTCAG*AATAAA*TTGAGAAGTCCAAAAAAAAAAAAAAAAAAAAAAAAAA
```

FIG.1A ( Cont'd )

```
              10         20         30         40         50         60
         ....|....|....|....|....|....|....|....|....|....|....|....|
hIL-17RLM-L   1 MAPWLQLCSVFPTVNACLNGSQLAVAAGGSGRARGADTCGWRGVGPASRNSGLYNITFKY
hIL-17RLM-S   1 ------------------------------------------------------------

70         80         90        100        110        120
         ....|....|....|....|....|....|....|....|....|....|....|....|
hIL-17RLM-L  61 DNCTTYLNPVGKHVIADAQNITISQYACHDQVAVTILWSPGALGIEPLKGPRVILEELKS
hIL-17RLM-S   1 ------------------------------------------------------------

130        140        150        160        170        180
         ....|....|....|....|....|....|....|....|....|....|....|....|
hIL-17RLM-L 121 EGRQCQQLILKDPKQLNSSFKRTG MESQPFLNMKFETDYFVKVVPFPSIKNESNYHPFFF
hIL-17RLM-S   1 ------------------------MESQPFLNMKFETDYFVKVVPFPSIKNESNYHPFFF 190        200        210        220        230        240
         ....|....|....|....|....|....|....|....|....|....|....|....|
hIL-17RLM-L 181 RTRACDLLLQPDNLACKPFWKPRNLNISQHGSDMQVSPDHAPHNFGPRFFYLHYKLKHEG
hIL-17RLM-S  37 RTRACDLLLQPDNLACKPFWKPRNLNISQHGSDMQVSPDHAPHNFGPRFFYLHYKLKHEG 250        260        270        280        290        300
         ....|....|....|....|....|....|....|....|....|....|....|....|
hIL-17RLM-L 241 PFKRKTCEQEQTTEMTSCLLQNVSPGDYIIELVDDTNTTRKVMHYALKPVHSPWAGPIRA
hIL-17RLM-S  97 PFKRKTCEQEQTTEMTSCLLQNVSPGDYIIELVDDTNTTRKVMHYALKPVHSPWAGPIRA 310        320        330        340        350        360
         ....|....|....|....|....|....|....|....|....|....|....|....|
hIL-17RLM-L 301 VAITVPLVVISAFATLFTVMCRKKQQENIYSHLDEESSESSTYTAALPRERLRPRPKVFL
hIL-17RLM-S 157 VAITVPLVVISAFATLFTVMCRKKQQENIYSHLDEESSESSTYTAALPRERLRPRPKVFL 370        380        390        400        410        420
         ....|....|....|....|....|....|....|....|....|....|....|....|
hIL-17RLM-L 361 CYSSKDGQNHMNVVQCFAYFLQDFCGCEVALDLWEDFSLCREGQREWVIQKIHESQFIIV
hIL-17RLM-S 217 CYSSKDGQNHMNVVQCFAYFLQDFCGCEVALDLWEDFSLCREGQREWVIQKIHESQFIIV 430        440        450        460        470        480
         ....|....|....|....|....|....|....|....|....|....|....|....|
hIL-17RLM-L 421 VCSKGMKYFVDKRNYKHKGGGRGSGKGELPLVAVSAIAEKLRQAKQSSSAALSKFIAVYF
hIL-17RLM-S 277 VCSKGMKYFVDKRNYKHKGGGRGSGKGELPLVAVSAIAEKLRQAKQSSSAALSKFIAVYF 490        500        510        520        530        540
         ....|....|....|....|....|....|....|....|....|....|....|....|
hIL-17RLM-L 481 DYSCEGDVPGILDLSTKYRLMDNLPQLCSHLHSRDHGLQEPGQHTRQGSRRNYFRSKSGR
hIL-17RLM-S 337 DYSCEGDVPGILDLSTKYRLMDNLPQLCSHLHSRDHGLQEPGQHTRQGSRRNYFRSKSGR 550        560        570        580        590        600
         ....|....|....|....|....|....|....|....|....|....|....|....|
hIL-17RLM-L 541 SLYVAICNMHQFIDEEPDWFEKQFVPFHPPLRYREPVLEKFDSGLVLNDVMCKPGPESD
hIL-17RLM-S 397 SLYVAICNMHQFIDEEPDWFEKQFVPFHPPLRYREPVLEKFDSGLVLNDVMCKPGPESD 610        620        630        640        650        660
         ....|....|....|....|....|....|....|....|....|....|....|....|
hIL-17RLM-L 601 FCLKVEAAVLGATGPADSQHESQHGGLDQDGEARPALDGSAALQPLLHTVKAGSPSDMPR
hIL-17RLM-S 457 FCLKVEAAVLGATGPADSQHESQHGGLDQDGEARPALDGSAALQPLLHTVKAGSPSDMPR 670        680        690        700        710        720
         ....|....|....|....|....|....|....|....|....|....|....|....|
hIL-17RLM-L 661 DSGIYDSSVPSSELSLPLMEGLSTDQTETSSLTESVSSSSGLGEEEPPALPSKLLSSGSC
hIL-17RLM-S 517 DSGIYDSSVPSSELSLPLMEGLSTDQTETSSLTESVSSSSGLGEEEPPALPSKLLSSGSC

730
         ....|....|....|....
hIL-17RLM-L 721 KADLGCRSYTDELHAVAPI  739
hIL-17RLM-S 577 KADLGCRSYTDELHAVAPI  595
```

FIG. 1B

```
IL-17AR    353 EKYSDDTKYTDGLPAADLIPPLKPRKVWIIYSA-DHPLYVDVLKFAQFLLTACGIEVA
                E+ S+ + YT  LP  L P   KV++ YS+ D   +++VV  FA FL   CG EVA
hIL-17RLM-L 335 EESSESSTYTAALPRERLRERP----KVFLCYSSKDGQNHMMVVQCFAMFLQDFCGCEVA

IL-17AR    412 LDLIEEQAISEAGVMTWVGRQKQEMVESNSKIIVLCSRGTR----AKWQALIGRGAPVRL
                LDL E+ ++   G WV      + + + IIV+ CS+G +    K     G G
hIL-17RLM-L 391 LDLWEDFSLCREGQREWV----IQKIHESQFLIVVCSNGMKYFVDHKNYKHKGG-----

IL-17AR    468 RCDHGKPVGDLFTAPMNMILPDFKR-----RACFGTYVVCYESEVSCDGDVPDLFGAAPR
                    G+LF A++ I ++          A   ++ YE + SC+GDVP  +  + +
hIL-17RLM-L 442 ---RGSGKGELELVQVSAIAEKLRQAKQSSSAALSKFIAVYE-DYSCEGDVPGILDLSTK

IL-17AR    523 YPLMORFEEV--YFRIQDLEMPQPGRMHRVGELSGDNYLRSPGGRQLRAALDRFRDWQVR
                Y LMD  ++ +  +D + +PG+  RG  S    NY RS  GR L  A+    +
hIL-17RLM-L 498 YRLMDNLPQLCSHLESRDHGLQEPGQHTRQG--SRRNYFRSKSGRSLYVAICNMHQFIDE

IL-17AR    581 QPDWFE 586
                 PDWFE
hIL-17RLM-L 556 EPDWFE 561
```

FIG. 1C

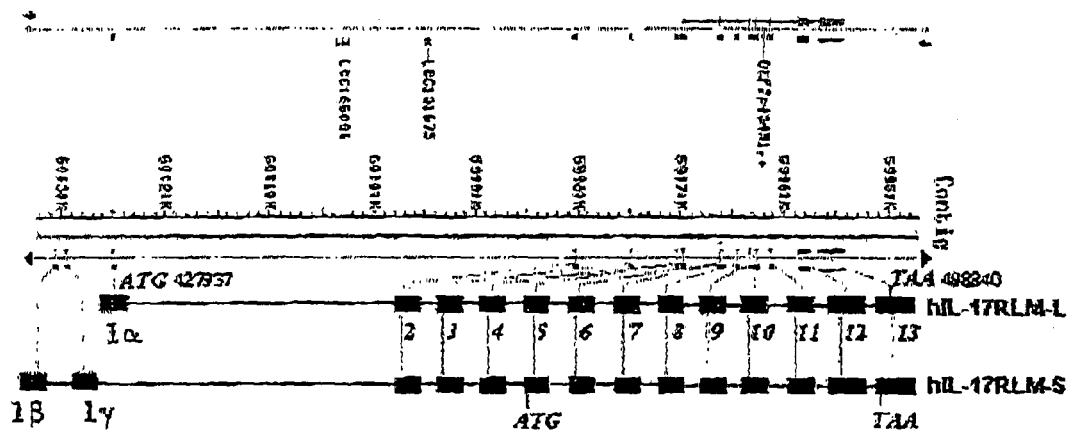

Fig. 1D

FIG. 2C
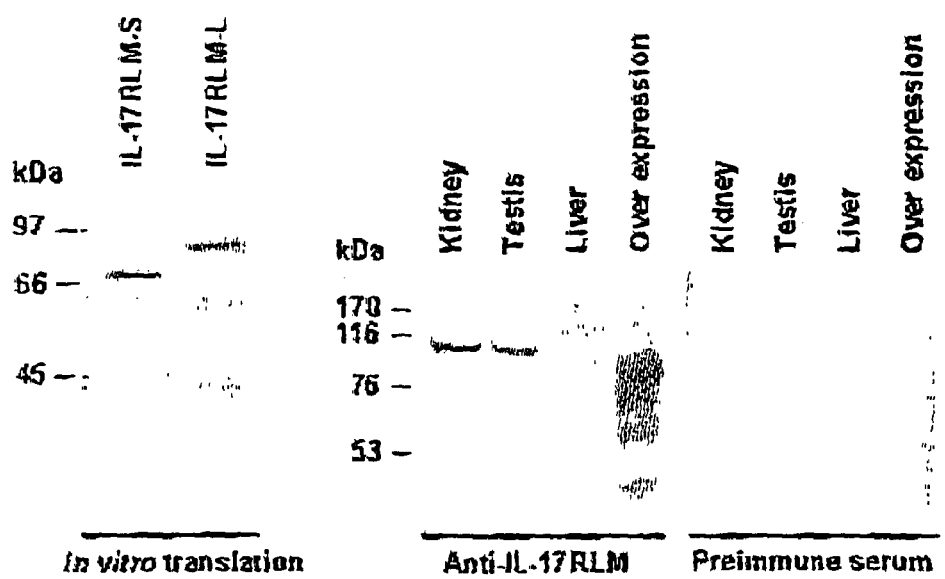
FIG. 2D
786-O cells        GRC-1
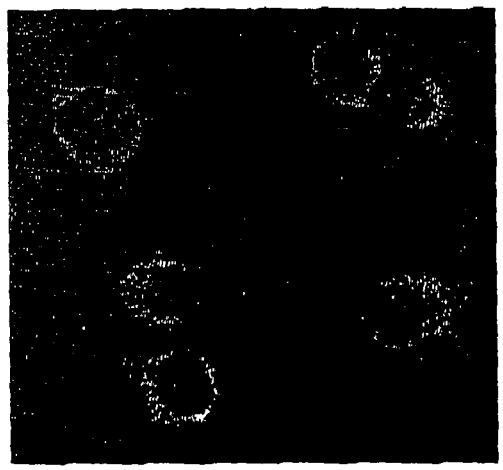

FIG. 3D
FIG. 3E
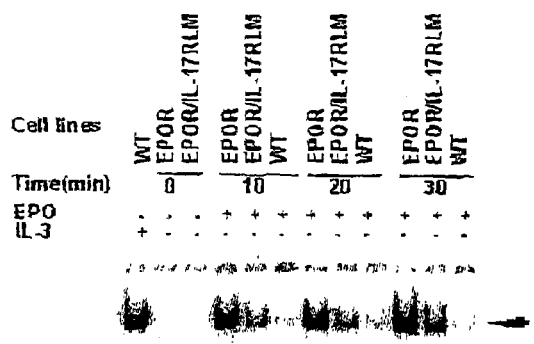
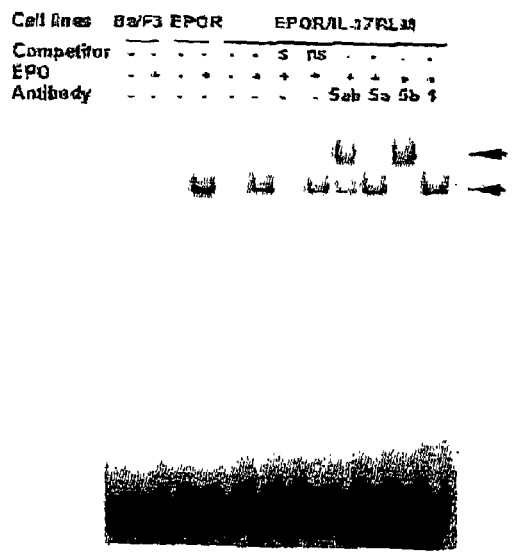

FIG. 4A
FIG. 4B
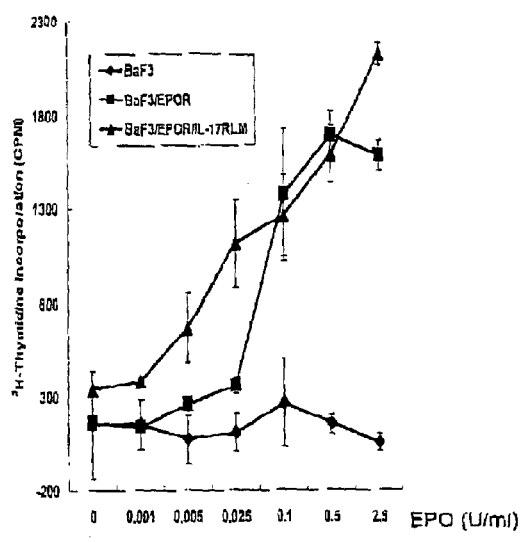
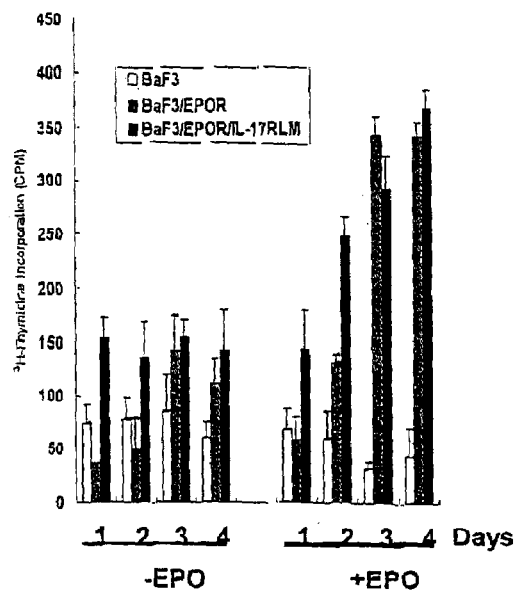

FIG. 6E
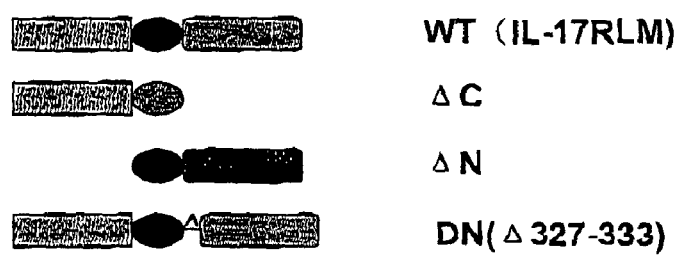
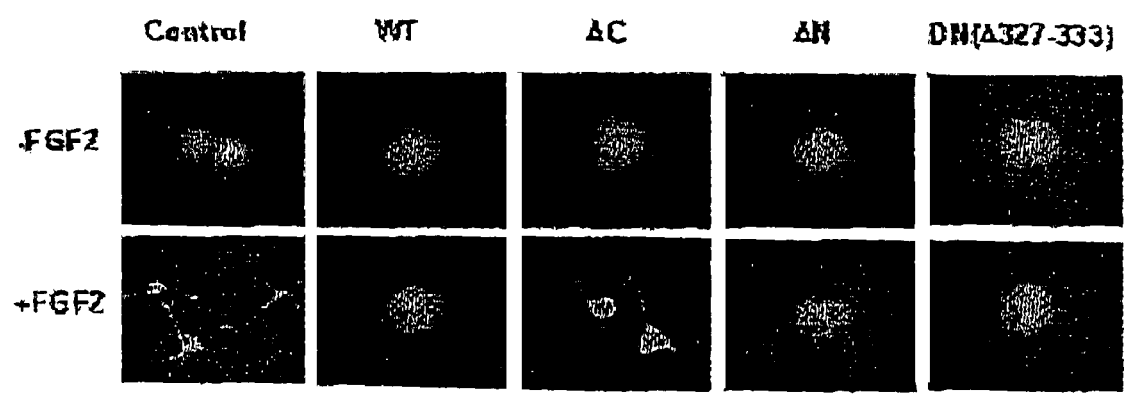

POLYNUCLEOTIDE ENCODING HUMAN INTERLEUKIN-17 RECEPTOR LIKE MOLECULE

FIELD OF INVENTION

The application relates to a newly identified polynucleotide, polypeptide encoded by such polynucleotide, the use of such polynucleotide and polypeptide, as well as the production of such polynucleotide and polypeptide. More particularly, the polypeptide of the present invention is human interleukin-17 receptor like molecule (IL-17RLM).

BACKGROUND

IL-17 is a T cell-derived cytokine that plays an important role in the initiation or maintenance of the proinflammatory response(1–5). Recently, four new proteins are identified and termed as IL-17B, IL-17C, IL-17E/IL-25 and IL-17F/ML-1/IL-26 that are clearly related to IL-17, suggesting that there exists a family of IL-17-like molecules (6–13).

Three homologous receptors for IL-17 family members are also identified, termed as IL-17 receptor, IL-17BR (also known as IL-17Rh1) and IL-17RL (14). IL-17 receptor (IL-17AR) located on human chromosome 22q11.22–11.23 is widely expressed in different tissues and is reported to bind to IL-17A with a weaker affinity than the potency of IL-17A on responsive cells. This receptor is shown to regulate the activities of extracellular regulated kinase ERK1, ERK2, c-Jun N-terminal kinase (JNK), p38 mitogen-activated protein kinase, Raf-1 kinase, STATs and NF-κB (15–20). Furthermore, the recent report that IL-17AR signaling is deficient in TRAF-6-deficient cells strongly suggests that members of the TRAF family, known to be involved in both IL-1/Toll and TNF receptor signaling, are also involved in IL-17AR signaling (21). The proinflammatory function and intracellular signaling pathway of IL-17AR are strikingly similar to those of the IL-1 and Toll receptors (22–26). IL-17BR (IL-17Rh1) located on human chromosome 3p21.1 is expressed mostly in liver and kidney tissues. This receptor binds to IL-17B and IL-17E but not IL-17A (8). Moreover this receptor is shown to activate NF-κB only by luciferase assay in vitro. IL-17RL located on human chromosome 3p25.3–3p24.1 is expressed mainly in prostate, cartilage, kidney, liver, heart, and muscle tissues (14), which has at least eleven splicing forms. However, the signaling mechanism and the biological functions of this receptor are still unknown.

Thus so, in an attempt to identify new IL-17 receptor like membrane proteins, the inventors have isolated and identified a novel single span transmembrane type 1 cytokine receptor-like protein with 31% amino acid identity to IL-17 receptor, and designated the new receptor as hIL-17RLM (IL-17 receptor like molecule).

SUMMARY OF THE INVENTION

In accordance with one aspect of the present invention, there is provided a novel polypeptide, as well as biologically active and diagnostically or therapeutically useful fragments thereof. The polypeptide of the invention is of human origin and designated as hIL-17RLM. hIL-17RLM has two alternative splicing forms, namely hIL-17RLM-L and hIL-17RLM-S, with an amino acid sequence of SEQ ID NO:2 and SEQ ID NO:4, respectively. hIL-17RLM-L shares a 75% amino acid sequence identity with hIL-17RLM-S.

In accordance with another aspect of the invention, there is provided an isolated polynucleotide encoding a polypeptide of the invention including mRNA, DNA, cDNA, genomic DNA as well as biologically active and diagnostically or therapeutically useful fragments thereof. Preferably, the polynucleotides encoding the two splicing forms of the hIL-17RLM of the invention, hIL-17RLM-L and hIL-17RLM-S, have the nucleotide sequence of SEQ ID NO:1 and SEQ ID NO:3, respectively.

In accordance with yet a further aspect of the present invention, there is provided a process for producing such polypeptide by recombinant techniques comprising culturing recombinant prokaryotic and/or eukaryotic host cells containing a nucleic acid sequence encoding a polypeptide of the present invention, under conditions promoting expression of said polypeptide and subsequent recovery of said polypeptide.

In accordance with yet a further aspect of the present invention, there is provided a process for utilizing such polypeptide, or polynucleotide encoding such polypeptide for therapeutic purposes. It is expected that the novel protein would be one promising therapeutic target in some diseases or carcinoma, such as rheumatoid arthritis, asthma, kidney or testis related carcinoma, and neuron diseases.

In accordance with yet a further aspect of the present invention, there are provided antibodies against such polypeptides.

In accordance with still another aspect of the present invention, there is provided nucleic acid probes comprising nucleic acid molecules of sufficient length to specifically hybridize to a nucleic acid sequence of the present invention.

In accordance with still another aspect of the present invention, there is provided a method for treating an individual in need of an increased level of IL-17RLM polypeptide activity in the body comprising administering to such an individual a composition comprising a therapeutically effective amount of an isolated IL-17RLM polypeptide of the invention or an agonist thereof.

In accordance with still another aspect of the present invention, there is provided a method for treating an individual in need of a decreased level of IL-17RLM polypeptide activity in the body comprising administering to such an individual a composition comprising a therapeutically effective amount of an IL-17RLM antagonist.

These and other aspects of the present invention should be apparent to those skilled in the art from the teaching herein.

BRIEF INTRODUCTION OF DRAWINGS

The following drawings are illustrative of embodiments of the invention and are not meant to limit the scope of the invention as encompassed by the claims.

FIG. 1. Sequence information of IL-17RLM, in which:
  A. Nucleotide and deduced amino acid sequence of interleukin-17 receptor like molecule(hIL-17RLM-L); B. Sequence alignment of IL-17RLM alternative splicing forms; C. Sequence alignment of human IL-17RLM and human IL-17 receptor; D. Genomic structure of human IL-17RLM FIG. 2. Expression of IL17RLM, in which:
  A. Tissue distribution of IL-17RLM mRNA; B. RT-PCR analysis for IL-17RLM expression; C. Endogenous expression of IL-17RLM protein in mouse tissues; D. Subcellular localizatin of the IL-17RLM protein; E. Immunohistochemical detection of IL-17RLM protein in various tissues.

FIG. 3. The activation of Stat5 signal pathway by IL-17RLM, in which:
(A) EPOR/hIL-17RLM chimeric receptor promotes STAT5 transcription activity; (B) EPOR/hIL-17RLM chimeric receptor mediates STAT5 tyrosine phosphorylation; (C) STAT5 DNA-binding activity was mediated by EPOR/IL-17RLM chimeric receptor upon stimulation of EPO; (D) EPOR/IL-17RLM chimeric receptor mediates STAT5 DNA-binding activity in a time course manner; (E) EPOR/IL-17RLM chimeric receptor mediates STAT5b DNA-binding activity.

FIG 4. Homodimerization of EPOR/IL-17RLM leads to the proliferation of Ba/F3 cells, in which
FIG. 4A shows that IL-17RLM cytoplasmic domain can transduce a proliferation signal in Ba/F3 cells in a dose dependent manner: and FIG. 4B shows the time course of proliferation.

FIG. 5. Interaction of hIL-17RLM-L with mFGFR, in which:
A. Co-immunoprecipitation of hIL-17RLM-L and mFGFR1; B. Co-immunoprecipitation of hIL-17RLM-L and mFGFR2; C. Endogenous colocalization of IL-17RLM with FGFR1 in some tissues; and D. Colocalization of IL-17RLM with FGFR2 in transfected Cos7 cells FIG. 6. Effects of hIL-17RLM-L on differentiation of PC12 cells, in which:
A and B, Stably expressed hIL-17RLM-L significantly inhibits FGF2 or NGF-induced PC12 cell differentiation; C and D, hIL-17RLM-L strongly inhibits FGF2 or NGF-induced PC12 cell differentiation even in higher stimulation or elongated exposure of FGF2 or NGF; E and F, The intracellular domain of IL-17RLM-L is the functional domain for the negative effect of hIL-17RLM-L on PC12 cell differentiation.

FIG. 7. Effects of hIL-17RLM-L on Ras-MAPK signal pathway during bFGF-induced differentiation of PC12 cells, in which:
A. The intracellular domain of IL-17RLM is the functional domain for the inhibitory effects of hIL-17RLM-L on Ras-MAPK signal pathway; B, C. Dose dependent effects of hIL-17RLM-L(WT) and N-terminal truncated hIL17RLM-L (ΔN) on Ras-MAPK signal pathway by luciferase assay; D, E. hIL-17RLM-L inhibits FGF2-induced ERK activation in PC12 cells by Western blotting assay.

FIG. 8. hIL-17RLM-L interferes with Ras-MAPK signalling by acting on the upstream molecules of Ras. Constituted activation was detected by immunoblotting. The whole lyasates of transfected cells with active MEK (B) or active Ras (D) were immunoblotted with anti-p-ERK, anti-ERK and anti-IL-17RLM rabbit polyclonal serum, respectively titutively active MEK (MEK1RF)(A, B) or constitutively active Ras (Ras G12V)(C, D) constructs were transiently co-transfected into PC12 cells with Elk-1 luciferase reporter plasmids or the increasing amounts of hIL-17RLM-L plasmid for 36 hrs. The luciferase activity was measured as described above. Additionally, ERK FIG. 9. Schematic representation of the signaling potential and biological events mediated by IL-17RLM. EPOR/IL-17RLM chimeric construct leads to STAT5b activation mediated by Jaks response to erythropoietin(EPO). The artificial homodimerization of the IL-17RLM cytoplasmic domain is sufficient for growth of Ba/F3 cells. Additionally, overexpression of full length IL-17RLM or the cytoplasmic domain could inhibit the FGF-induced PC12 cell differentiation possibly through the prevention of FGFR-Ras-MAPK signaling pathway. Our data show IL-17RLM interferes with Ras-MAPK signaling pathway by interacting with FGFR or acting on the up-stream signaling molecules of Ras.

DETAILED DESCRIPTION OF THE INVENTION

In accordance with an aspect of the present invention, there is provided a novel polypeptide, as well as biologically active and diagnostically or therapeutically useful fragments thereof. The polypeptide of the invention is of human origin and designated as hIL-17RLM. hIL-17RLM has two alternative splicing forms, namely hIL-17RLM-L and hIL-17RLM-S, with an amino acid sequence of SEQ ID NO:2 and SEQ ID NO:4, respectively. hIL-17RLM-L shares a 75% amino acid sequence identity with hIL-17RLM-S.

The term "fragment" when referring to the polypeptides of SEQ ID NO:2 or SEQ ID NO.4, means a polypeptide which retains essentially the same biological function or activity as such polypeptides.

The polypeptide of the present invention may be a recombinant polypeptide, a natural polypeptide or a synthetic polypeptide, preferably a recombinant polypeptide.

The potypeptides of the present invention include the polypeptide of SEQ ED NO:2, the polypeptide of SEQ ID NO:4 as well as polypeptides which have at least 70% similarity preferably at least 70% identity), and more preferably at least 90% similarity (more preferably at least 90% identity) and still more preferably at least 95% similarity (still more preferably at least 95% identity) to the polypeptide of SEQ ID NO:2 or SEQ ID NO:4. The terms "similaty"0 and "identity" are used herein with the meanings known in the art.

Computer-assisted analysis suggests that mature IL-17RLM-L contains a putative signal peptide of 16 amino acids, a 281-amino acid extracellular domain (C17-Pro297), a 23-amino acid transmernbrane stretch (Ile298-Met320), and a 420-amino acid longer cytoplasmic tail (Cys321-Leu739) than that of IL-17BR/IL-17Rh1. The cytoplasmic portion of this new receptor polypeptide of the invention is much longer than IL-17BR, and is comparable with the unusually long tail described for IL-17 receptor. Additionally, there are nine cystine residues in extracellular domain and eight potential N-linked glycosylation sites in the extracellular domain of the polypeptide of the invention. The extracellular domain also consists of a predicted immunoglobulin domain and a putative fibronectin III domain. This protein is predicted to be a type I membrane protein according to Hartmann membrane topology model and PSORT II server prediction. But there is no WSXWS (SEQ ID NO:20) motif, typical of type I receptor (32, 33) in the extracellular domain. The sequence of IL-17RLM-L is slightly atypical for type I cytokine receptors in that the usual WSXWS (SEQ ID NO:20) motif is replaced by WSPGA (SEQ ID NO:21). Furthermore, a segment (TPPPLRPRKVW (SEQ ID NO:22)) located proximal to the IL-17 receptor transmembrane domain, which is highly conserved among cytokine receptor, is replaced by the proline-rich motif (PFHPPPL-RYREP (SEQ ID NO:23)), which was a typical feature of a transactivation domain for transcription factors. Interestingly, both a putative TIR domain (Toll/IL-1-Receptor homology domain) and a putative SH3 interaction domain (proline-rich domain) were predicted in the intracellular domain of the protein from (V358 to K424). Additionally, a putative tyrosine phosphorylation site juxtapsed to the transmembrane domain (Y329) was also identified. The long COOH-terminal tail (C-tail) of IL-17RLM also contains multiple tyrosine residues and putative Stat binding motifs.

In accordance with another aspect of the present invention, there is provided an isolated nucleic acid which encodes the polypeptide having the amino acid sequence of SEQ ID NO:2 or SEQ ID NO:4.

The polynucleotide of the invention was discovered in normal human testes mRNA and 293T cells mRNA by 5'-RACE assay. It belongs to human IL-17 receptor family and has a higher similarity to IL-17R than that of all known IL-17 receptor homologues. At least two RNA splicing variants were found, transcribed from 13 exons localized on human chromosome 3p21.1, named by hIL-17RLM-L and hIL-17RLM-S, respectively. The longer isoform of IL-17RLM (IL-17RLM-L) contains an open reading frame encoding a polypeptide of 739 amino acid residues. The shorter isoform of IL-17RLM (IL-17RLM-S) contains an open reading frame encoding a polypeptide of 595 amino acid residues.

The polynucleotide of the present invention may be in the form of RNA or in the form of DNA, which DNA includes cDNA, genomic DNA and synthetic DNA. The DNA may be double-stranded or single-stranded and if single stranded may be the coding strand or the non-coding strand. The coding sequence which encodes the longer isoform IL-17RLM-L may be identical to the coding sequence shown in SEQ ID NO:1 or may be a different coding sequence which coding sequence, as a result of the redundancy or degeneracy of the genetic code, encodes the same polypeptide as the DNA of SEQ ID NO:1. The coding sequence which encodes the shorter isoform IL-17RLM-S may be identical to the coding sequence shown in SEQ ID NO:3 or may be a different coding sequence which coding sequence, as a result of the redundancy or degeneracy of the genetic code, encodes the same polypeptide as the DNA of SEQ ID NO:3.

The present invention further relates to polynucleotides which hybridize to the hereinabove-mentioned sequences if there is at least 70%, preferably at least 90%, and more preferably at least 95% identity between the sequences. The present invention particularly relates to polynucleotides which hybridize under stringent conditions to the hereinabove-mentioned polynucleotides. As herein used, the term "stringent conditions" means hybridization will occur only if there is at least 95% and preferably at least 97% identity between the sequences. The polynucleotides which hybridize to the above-mentioned polynucleotides in a preferred embodiment encode polypeptides which either retain substantially the same biological function or activity as the polypeptides encoded by the DNAs of SEQ ID NO:1 or SEQ ID NO:3.

The present invention also relates to vectors which include polynucleotides of the present invention, host cells which are transfected or transformed with vectors of the invention and the production of polypeptides of the invention by routine recombinant techniques.

Figure 6A:
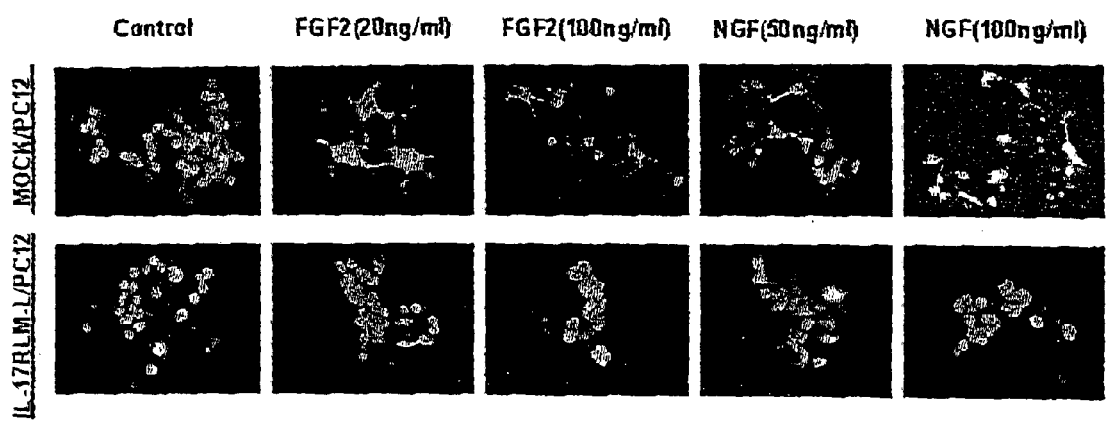

The present invention also relates to diagnostic or therapeutic uses of the polypeptide of the invention. As shown in the Examples, the polypeptide of the invention is highly expressed in kidney or testis related carcinoma tissues. Therefore, the polypeptide or its encoding polynucleotide may be employed as a diagnostic marker in detecting these cancers. Furthermore, as shown in FIG. 6A, stably expressed hIL-17RLM-L significantly inhibits FGF2 or NGF-induced rat pheochromocytoma PC12 cell differentiation, so the polypeptide of the invention may be useful in treating neuron diseases. Additionally, being similar to IL-17 receptor which is known to be involved in autoimmune diseases such as rheumatoid arthritis and asthma, the polypeptide of the invention may be antagonized so as to treat these diseases. Preferably, the antagonist is an antibody. Alternatively, antisense technique may be employed to prevent the in vivo expression of the polypeptide of the invention so as to treat these autoimmune diseases.

The present invention will be further described with reference to the following examples; however, it is to be understood that the present invention is not limited to such examples.

EXAMPLES

In the examples, the following experimental procedures are used to clone and identify the polynucleotide of the invention and to test the functions of the polypeptide of the invention:

Genebank database search and RACE PCR The human high-throughput genomic sequence was scanned for "virtual" ORFs by using ab initio gene prediction program GENSCAN (30). The signal sequence was predicted by SIGNALP algorithm(31). Transmembrane predictions were performed with TMPRED (32), an algorithm based on the statistical analysis of a transmembrane domain databas pT-A e, as well as TMHMM algorithm. Netphos2.0 was used to identify and score all possible cytoplasmic serine, threonine and tyrosine phosphorylation sites. To obtain a full length of cDNA, 5'-RACE PCR was performed using mRNA from normal human testis and 293T cells according to SMARTT-MRACE cDNA amplification kit user manual (CLONTECH). Total RNA was extracted by using with TRIzol reagent kit (Life Technologies, Inc) and reverse transcribed by using an oligo (dT) primer and superscript II (Life Technologies, Inc). The 5'-RACE PCR products were then cloned into dv vector according to AdvanTageTMPCR cloning kit instructions and then sequenced.

Cell lines THP-1 is a human acute monocytic leukemia cells. Jurkat and 6T-CEM are T cell acute lymphocytic leukemia cell lines. K562 is an erythroleukemia cell line U937 is human leukemia cell line. 786-O is a renal cell adenocarcinoma cell line. GRC-1 is a granular renal carcinoma cell line. THP-1, Jurkat, 6T-CEM, K562, U937 and 786-O cells were maintained in RPMI 1640 supplemented with 10% FBS, 2 mM L-glutamine/penicillin/streptomycin (Life Technologies, Inc) at 37° C. under 5% CO2. GRC-1, HepG2, A431, 293T cells and COS7 cells were maintained in DMEM containing 10% FBS/glutamine/penicillin/streptomycin. Ba/F3 is a murine IL-3-dependent pro-B cell line, and grown in RPMI complete medium containing 5×10−5 M 2-mercaptoethanol and 5% WEHI-3B-conditioned medium as a source of IL-3. Rat pheochromocytoma PC12 cells (ATCC: CRL-1721) were maintained in Dulbecco's modified Eagle's medium (DMEM) supplemented with 10% fetal calf serum and 5% horse serum (Life Technologies, Inc).

Antibody preparation For bacterial production of hIL-17RLM, an open reading frame coding for the peptide in intracellular domain of hIL-17RLM ($M^{320}$-$I^{457}$, 138aa) was amplified by PCR and cloned into pGEX4T-1 vector. The reading frame was sequence-confirmed following cloning. hIL-17RLM was expressed in the inclusion bodies in E.coli and solubilized with 4 M guanidine HCL and dialyzed against 50 mM sodium acetate buffer, pH5, containing 0.1 M NaCl. Antisera were raised in rabbits by standard methods and used for immunoblot analysis after 1000 to 10000-fold dilution.

Immunofluorescent staining and microscopy 786-O and GRC-1 cells were cultured on 6-well plate with $8 \times 10^4$ per well (Corning Incorporated Corning, N.Y.). One day later, cells were washed in PBS and fixed with 4% formaldehyde in PBS for 20 minutes. Then, the cells were permeability with 0.5% Triton X-100 in PBS for 10 minutes. Cells were blocked with 10% normal goat serum in PBS for 1 hour and then incubated with 1:1000 diluted anti-IL-17RLM-antibody for 1 hour. After washed with 0.1% Tween-20 in PBS, cells were incubated with 1:100 diluted FITC-labeled goat anti-rabbit Ig G (Santa Cruz Biotechnology; Inc) in PBS. After incubated for 1 hour, cells were washed with 0.1% Tween-20 in PBS again. The cells were viewed using Nikon inverted microscope ECLIPSE TE300.

Generation of Stably Transfected Ba/F3 and PC12 Cell Clones

The murine EPOR cDNA was obtained from Harvey Lodish's lab, and cloned into pIRESneo expression plasmid by PCR amplification with primers as follows: sense, 5' TATAGCGATATCATGGACAAACTCAGGGTGCC 3' (SEQ ID NO:5), antisense, 5' AATGAATTCC TAGGAG-CAGGCCACATAGCC 3' (SEQ ID NO:6). Full length cDNA of human IL-17RLM-L was cloned into pcDNA3 expression plasmid with primers as follows: sense, 5' ATAAAGCTTATGGCCCCGTGGCTGC 3' (SEQ ID NO:7), antisense, 5' TTCTCGAGTTACAAAGGGGC-GACCGC 3' (SEQ MD NO:8). Chimeric construct of EPOR/IL-17RLM containing the extracellular and transmembrane domain of EPOR and intracellular domain of hIL-17RLM was prepared by PCP, amplification with specific primers as follows: for EPOR (extracellular domain), sense, 5' TATAGCGATATCATGGACAAACT-CAGGGTGCC 3' (SEQ ID NO:9), antisense, 5' TATA-GAATTCCAGCAGGGCCAGAACCGTC 3' (SEQ ID NO:10), for hIL-17RLM (intracellular domain), sense. 5' ATTGAATTCTGCCGCAAGAAGCAAC 3' (SEQ ID NO:11), antisense, 5' ATTGGATCCTTACAAAGGGGC-GACCCC 3' (SEQ ID NO:12). Above constructs (20 µg) were stably introduced into $10^7$ Ba/F3 cells by electroporation using a BTX machine at 240 V and 1050 µF. Twenty-four hours after electroporation, cells were re-plated in growth medium supplemented with 1 mg/mL of G418. G418 resistant cells were kept in medium with IL-3 and G418 or switched to a given cytokine at the indicated concentration: human IL-3, 5 ng/mL, rhEPO, 2 U/mL. The selected positive clones were confirmed by Northern blot and immunoblotting.

To establish hIL-17RLM-L or EPOR/IL-17RLM stably expressed PC12 cell lines, PC12 cells were transfected with above constructs using with Transfast transfection reagent (Promega). Forty-eight hours post-transfection, cells were plated at several different dilutions in media containing 0.5 mg/ml G418. For the next two weeks, the selective media were replaced every 3 to 4 days. Once the distinct "islands" of surviving cells were visualized, the individual clones were transferred into 96 well plates and continued to maintain cultures in selected media. The positive clones were confirmed by immunoblotting.

Northern blot analysis and reverse transcription-PCR analysis Multiple tissue blots containing poly (A)+RNA (2 µg per lane) from various human tissues were purchased from CLONTECH. A fragment of IL-17RLM coding regions was used as hybridization probe. DNA probes were labeled with [$\alpha$-$^{32}$P] dCTP according to Prime-a-Gene® labeling system instructions(Promega). Labeled nucleotides were purified using with MicroSpin™G-50 columns (Amersham Pharmacia Biotech). Hybridization was performed with Expresshyb (CLONTECH) at 68° C. for 1 hr. The blots then were washed with 2×SSC/0.05% SDS solution at room tempcrature for 40 min, followed by washing in 0.1×SSC/0.1% SDS solution at 50° C. for 40 min with one change of fresh solution. The blots were exposed in Phosphor Imager for 24 hrs. DNA probes from blots were strapped by incubating the blot in sterile $H_2O$ containing 0.5% SDS at 100° C. for 20 min. Then the membrane was additionally blotted by β-actin probe as internal control.

Total RNA from all selected cell lines was extracted using with TRIzol reagent, according to the manufacturer's recommendations (life Technologies). RT-PCR was performed on 0.5 µg of total RNA with an oligo (dT) primer according to QIAGEN®OneStep RT-PCR kit handbook instructions. cDNA was amplified for 35 cycles with primers specific for the CDS of human IL-17RLM as follows: sense 5'-ATAG-GTACCATGGAATCTCAACCTTTCCTG-3' (SEQ ID NO:13) and antisense 5'-ATAGGATCCCAAAGGGGC-GACCGCG-3' (SEQ ID NO:14). Then the nested PCR reactions were performed using previous PCR products as a template with primers specific for a 500 bp coding region of human IL-17RLM cDNA as follows: sence 5'-CGTGGTAC-CGATGGAATCTCkACCTTTCCTG-3' (SEQ ID NO:15) and antisense 5'-ATATCTAGAGGGCCCGGCCCACGG-3' (SEQ ID NO:16). The upstream primer of human β-actin is 5'-AGCTCACCATGGATGATGATATC-3' (SEQ ID NO:17), and its downstream primer is 5'-TGTTGAAG-GTCTCAAACATGATCT 3' (SEQ ID NO:18), with the expected product of 394 bp. The PCR products were subjected to electrophoresis on 1.8% ethidium bromide-stained agarose gel, then transferred to nylonmembrane, and probed with a $^{32}$P-labeled cDNA probe specific for IL-17RLM.

Preparation of nuclear and non-nuclear protein fractions EPO-stimulated cells were washed and scraped into phosphate-buffered solution and centrifuged at 4.500 rpm for 5 min in a microfuge. The cells were suspended in buffer (10 mM Tris, pH 7.5, 1.5 mM $MgCl_2$, 10 mM KCl, 0.5% Nonidet P-40) at about 10× the packed cell volume and lysed by gentle pipetting. Nuclei were recovered by microcentrifugation at 7,000 rpm for 5 min. The supernatant, which represents the cytoplasmic and membrane protein fraction, was collected and stored at −80° C. Nuclear proteins were extracted at 4° C. by gentle suspension of the nuclei (at about 2× the packed nuclear volume) in buffer containing 20 mM Tris (pH 7.5), 10% glycerol, 1.5 mM $MgCl_2$, and 420 mM NaCl, 0.2 mM EDTA, followed by 30 min of platform rotation. The nuclear protein suspension was cleared by centrifugation at 13,000 rpm for 15 min. The supernatants were collected and frozen at −80° C. or directly used in gel shift assays. All buffers contained the following additions: 1–2 µg/ml each of aprotinin, leupeptin, pepstatin, 0.2 mM PMSF, 0.5 mM DTT, 10 mM NaF and 0.1 mM Na-vanadate. All steps were carried out on ice or at 4° C. Protein amounts were kept in the same for different treatments after measured by BCA protein assay (PIERCE), using BSA as a standard.

Electrophoretic mobility-shift assay DNA probes [double-stranded β-casein promoter GAS (γ-interferon activated sequence): 5'-AGATTTCTAGGAATTC-3' (SEQ ID NO:19)] were prepared by end-labeling with [γ-$^{32}$P]ATP and T4 polynucleotide kinase and purified by G-50 MicroSpin columns. Cells were washed three times in PBS and starved in the absence of cytokines for 8 hrs in RPMI 1640. Cells were then stimulated for the indicated times with the indicated cytokine at a concentration used in growth medium. Typically, 5 µl (10–20 µg) of nuclear proteins was incubated with 100,000 cpm of $^{32}$P-labeled oligonucleotides for 2 hrs at room temperature. The nuclear proteins and various oligonucleotide probes were incubated in buffer containing 10 mM Tris (pH 7.5), 10% glycerol, and 0.2% Nonidet P-40. Additionally, 2–4 µg of poly (dI-dC) was included as a nonspecific competitor DNA. Protein-DNA complexes were resolved on 4% nondenaturing polyacrylamide gels in 0.5× TBE running buffer. After electrophoresis, gels were dried and subjected to autoradiography. Antibody supershift experiments were carried out by addition of 4 µl of various antibodies purchased from Santa Cruz Biotechnology.

Western blotting and immunopricipitation The cells were lysed in lysis buffer containing 50 mM Tris, pH 7.6, 150 mM NaCl, 1% NP-40 and 1 mM sodium orthovanadate in the presence of protege inhibitors. The immune complexes were captured with protein A or G Sepharose, washed in lysis buffer and resolved by SDS-PAGE. The proteins were transferred onto nitrocellulose membrane and the membrane was blocked with 5% non-fat milk in PBS-buffered saline containing 0.1% Tween-20 overnight at 4° C. and then incubated the indicated primary antibody followed by horseradish-peroxidase-conjugated rabbit anti-sheep or anti mouse antibodies as secondary antibodies and detected by chemoluminescence according to manufacturer's instructions (ECL; Amersham).

Luciferase assay 4FTKSLN-Luc is a STAT5-responsive luciferase reporter plasmid. This construct contains 4 copies of IGAS sequence inserted upstream of a luciferase gene controlled by the thymidine kinase (TK) promoter. As an internal control, we used the pRL-TK vector (Promega) containing the Renilla luciferase gene under the control of the TK promoter. Cos7 cells were seeded into 12-well plates at a density of $5 \times 10^4$ cells/well, and transfected by SuperFect®Transfection reagent (Qiagen) with the indicated constructs. The amounts of transfected DNA were kept constant in all transfections. After 36 hrs of transfection, the cells were stimulated with or without 2 U/ml of recombinant human EPO (R&D Systems, Inc) for 30 min. Cells were collected and lysed for measurement of arbitrary luciferase activities. Luciferase activity was monitored with the Dual-Luciferase Reporter assay System kit (Promega). Each experiment was repeated three times. Data were normalized by co-transfection with Renilla luciferase reporter vector and expressed as mean±S.D.(n=3).

The Elk-1 luciferase activity assay was performed using trans-reporting constructs including PFA-Elk-1 and PFR-luciferase plasmids (PathDetect in vivo signal transduction pathway trans-reporting system, Stratagene) according to the manufacture instructions. The Elk-1 luciferase activity was measured using a Luciferase Assay System (Promega). The results were expressed as mean±S.D. From three independent experiments.

Cell proliferation assay DNA replication was analyzed by incorporation of [methyl-$^3$H] thymidine (Amersham Pharmacia Biotech). Typically, Ba/F3, Ba/F3/EPOR and BA/F3/EPOR/IL-17RLM cells were washed three times in PBS, then plated into 96 well-plate ($2 \times 10^4$ cells/200 µl/well) and starved for 8 hrs in RPMI 1640 medium containing 5% FCS, treated with the indicated concentration EPO for 72 hrs. [Methyl-$^3$H] thymidine was added into the medium for 4 hrs-[$^3$H] thymidine incorporation was measured by Microplate Scintillation & Lumninescence Counter (Packard). For time course and dose dependence cell proliferation experiments, 5,000 cells/200 µl/well were stimulated with or without 0.5 U/ml of EPO for various time. Experiments were performed in triplicate.

Differentiation of PC12 cells PC12 cells were maintained in DMEM supplemented with 10% fetal calf serum, 5% horse senum, and 4.5 g/L glucose at 37° C. under 5% $CO_2$. The cells were plated at a sub-confluent density on 12-well culture plates coated with poly-L-lysine to improve cell attachment activity. The next day, cells were transiently transfected with EGFP, wild type IL-17RLM-L and the mutants for 36 hrs using Effectene™ Transfection reagent (Qiagen). Cells were stimulated with or without 20 ng/ml of recombinant human FGF2 (R&D) for 72 hrs, then examined by fluorescence microscope. Cells with processes longer than 1.5 times the diameter of the cell body were considered to be positive for neurite outgrowth. The numbers of undifferentiated and differentiated cells were counted in three randomly selected fields, containing approximately 200 cells each. Data were expressed as means±S.D of three independent counts.

Immunohistochemistry Various normal human tissues were from the surgery of different patients in The First People's Hospital, Peking Medical University. All tissue specimens were formalin-fixed and paraffin-embedded. Rabbit polyclonal antibody (anti-intracellular domain of hIL-17RLM) generated was used. DAKO EnVision™, well suited for a two step immunohistochemistry procedure, was used for immunohistochemistry assay according to the kit instructions. The color development (varying from 10–30 min) was stopped under microscopic examination by adding a mixture of 10 mM Tris-HCl (pH 8.0) and 1 mM EDTA. The slides were mounted immediately. Pre-immune serum was used as control for each sample.

EXAMPLE 1

Cloning and Primary Structure of hIL-17RLM

To explore the existence of additional members of the IL-17 receptor family, we screened the EST database and the NR database in NCBI Gene Bank using the cytoplasmic domain of IL-17 receptor by tBlastn and Blastp algorithm. We found several ESTs encoding an unknown protein reported in the Gene Bank as hypothetical human protein DKFZp434N1928 (AL133097). However this sequence was only a fragment without N-terminus. Then we performed 5'-RACE PCR assay using the mRNA from the human testis tissue and 293T cells, and obtained two complete cDNAs with 4477 bp and 4478 bp in length. The full length ORF of 4477 bp sequence encoded a novel single transmembrane protein of 739 amino acids (FIG. 1A), while the other cDNA encoded a protein of 595 amino acids, which was a truncated form, lacking 144 amino acids at the N-terminus compared with the 739-aminl acid protein (FIG. 1B). BLAST analysis revealed that the most related protein with the two novel proteins was IL-17 receptor (IL-17AR). So the two proteins were named as human IL-17 receptor like molecule long form (hIL-17RLM-L) and short form (hIL-17RLM-S), respectively. The pair-wise comparison of the protein sequences of hIL-17RLM-L and hIL-17AR by BLASTP algorithm using BLOSUM62 scoring matrix showed that hIL-17RLM-L shared 31% identities (47% similarities) to hIL-17AR (FIG. 1C). Additionally, hIL-17RLM was mapped on human chromosome 3p21.1. Genomic structure analysis showed that hIL-17RLM-L was comprised of 13 exons and spanned 70903 base pairs, while hIL-17RLM-S consisted of 14 exons and spanned 85485 base pairs (FIG. 1D). Both of the sequences were submitted to Gene Bank with the accession number of AF494208 and AP494211, respectively.

We also cloned the mouse orthologeus of the gene named as mIL-17RLM-L and mIL-17RLM-S with 738 and 594 amino acids, respectively. The Gene Bank accession numbers are AF494210 and AF494209. hIL-17RLM-L shared 75% of identities to mIL-17RLM-L at amino acids level. mIL-17RLM-L was located on chromosome 14 with 13 exons and spanned 66304 base pairs. However mIL-17RLM-L was identical to the newly defined mSef gene, which shared 46% of identities with zSef gene(27, 28).

Computer-assisted analysis suggested that hIL-17RLM-L contained a putative signal peptide of 16 amino acids, a 281-amino acid extracellular domain ($C^{17}$-$Pro^{297}$), a 23-amino acid transmembrane stretch ($Ile^{298}$-$Met^{320}$), and a 420-amino acid cytoplasmic tail ($Cys^{321}$-$Leu^{739}$). The cytoplasmic portion of this new receptor was much longer than that of IL-17BR, and comparable with the unusually long tail of IL-17AR. This protein was predicted to be a type I cytokine receptor according to Hartmann membrane topology model and PSORT II server. However, hIL-17RLM-L had a WSPGA (SEQ ID NO:21) instead of WSXWS (SEQ ID NO:20) motif, which is a typical motif in the extracellular domain of type I cytokine receptors (33, 34) . There were eight cystine residues and nine potential N-linked glycosylation sites in the extracellular domain, where an immunoglobulin domain and a fibronectin III domain were also predicted. Furthermore, a highly cytokine receptor conserved segment (TPPPLRPRKVW (SEQ ID NO:22)) located proximal to the IL-17 receptor transmembrane domain was replaced by the proline-rich segment (PFHPPPLRYREP (SEQ ID NO:23)), a putative SH3 interaction domain, which was a typical feature of a transactivation domain for transcription factors. Additionally, a putative TIR domain ($V^{358}$ to $K^{424}$) (Toll/IL-1Receptor domain) and a putative TRAF6 binding motif ($P^{347}$ to $L^{351}$), Pro-X-Glu-X-X (aromatic/acidic residue) were predicted in the intracellular portion of hIL-17RLM-L. The TRAF6 binding motif was found in TRANCE-R and IRAK adapter kinases for ILR/Toll-like receptor signaling(35), suggesting that hIL-17RLM may play a role in the Toll-like receptor signaling. The long COOH-terminal tail (C-tail) of hIL-17RLM also contained multiple tyrosine residues. All of these implied that the protein might be a novel signaling receptor.

EXAMPLE 2

Cellular and Tissue Distribution of the hIL-17RLM

To gain insight into the potential function of this receptor, we examined the tissue distribution of this receptor by Northern blot using an open reading frame-specific probe for hIL-17RLM As shown in FIG. 2A, the mRNA was abundant with two specific transcripts of ~8.5 kb and ~4.5 kb in testis and kidney tissues. However, transcripts were detected at lower levels in brain, spleen, heart and uterus, and barely detected in lung, thymus and peripheral blood lymphocytes.

Figure 2B:
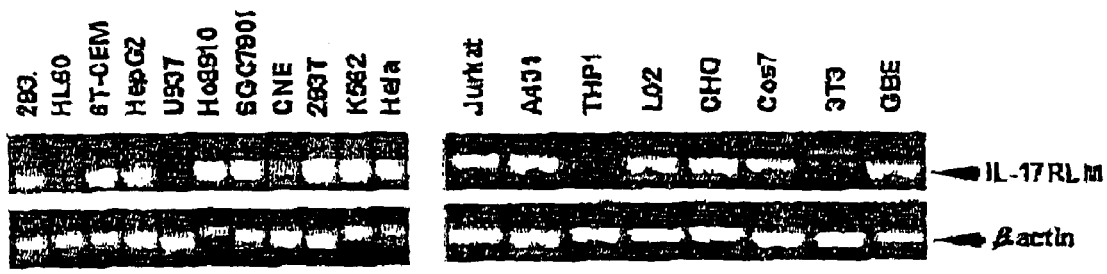

To observe the IL-17RLM mRMNA levels in different cells, we carried out RT-PCR analysis. As shown in FIG. 2B, mRNA of IL-17RLM was observed in most tumor and normal cell lines, including Jurkat, A431, GBE, 6T-CEM, K562, Hela, Ho8910, SGC7901, CNE, HepG2, 293, L02, CHO, COS1, but not HL60, THP-1, and U937 cell lines. However, IL-17RLM mRNA was hardly detected in those cell lines by Northern blot (data not shown), suggesting that IL-17RLM was weakly expressed in these cell lines.

The predicted molecular masses of hIL-17RLM-L and hIL-17RLM-S were 82 kD and 67 kD, respectively. A single specie of approximately 85 kD or 70 kD was observed respectively when hIL-17RLM-L or hIL-17RLM-S construct was translated in vitro. (FIG. 2C, left). In order to monitor hIL-17RLM expression in vivo, a rabbit polyclonal antiserum against a fragment of intracellular domain of hIL-17RLM was generated and used for Western blot. The data showed that the protein was approximately 100 kD, which was larger than the in vitro translated products. This was consistent with many N-linked glycosylation sites in the extracellular domain of hIL-17RLM-L (FIG. 2C, right).

To examine the subcellular location of hIL-17RLM proteins, we carried out immunostaining assay in a renal cell adenocarcinoma cell line 786-O and a granuler renal carcinoma cell line GRC-1 using the rabbit polyclonal antiserum. The data showed that the novel protein was mainly localized in the cell membrane (FIG. 2D).

Figure 2E:
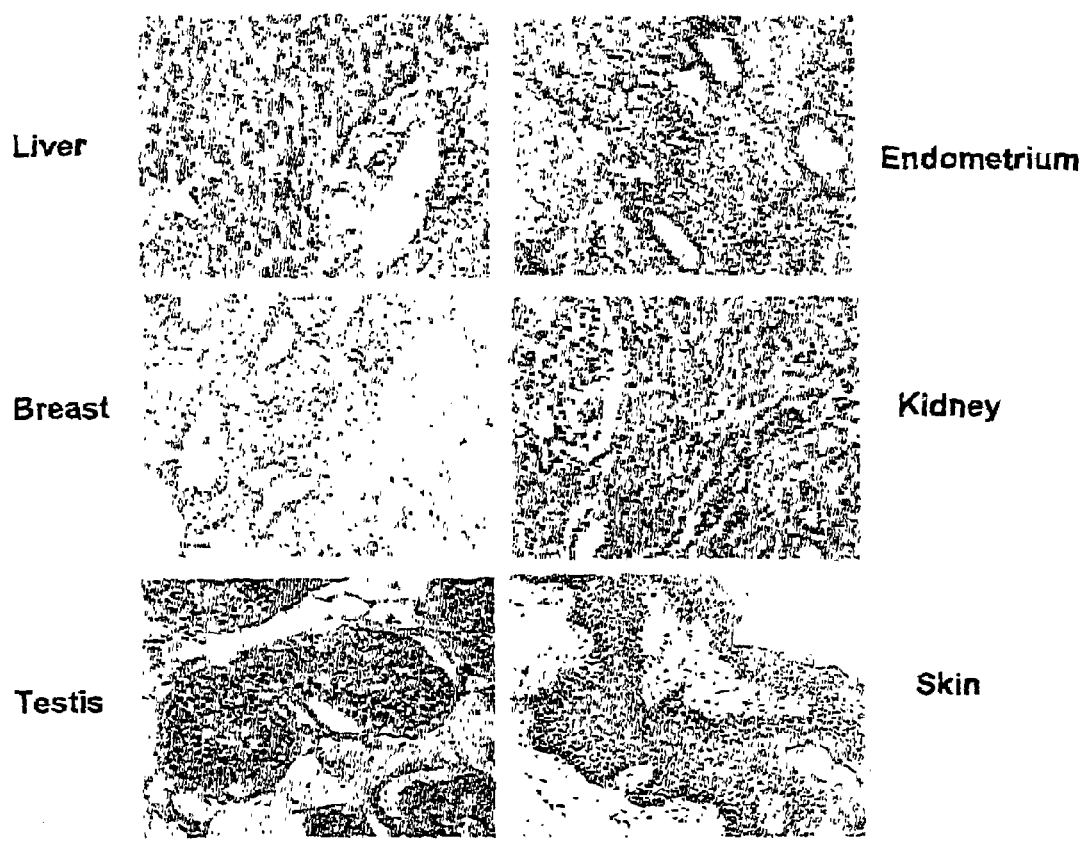

To investigate the hIL-17RLM protein expression in different human normal tissues, we carried out immunohistochemical assay using the rabbit polyconal antiserum. The data showed that hIL-17RLM protein was mainly expressed in kidney, testis and liver, but not detectable in breast, skin and endometrium (FIG. 2E). Interestingly, hIL-17RLM protein was specifically expressed in some types of cells in the process of spermatogenesis. IL-17RLM protein was detected in spermatogonia, spermatocytes and spermatids in testis. However, it was not detectable in spindle-shaped myofibroblasts and fibroblasts in the basement membrane of the seminiferous tubule. Also, it was negative result in Leydig cells in the supporting tissue of testis. In the blood vessels of testis, hIL17-RLM was not expressed in the smooth muscle cells but weakly detected in endotheliocytes. In kidney, hIL-17RLM protein was mainly expressed in the proximal convoluted tubule. It was not detected in the capillaries but weakly expressed in the mesangium in the renal corpuscle. In liver, it was clear that hIL-17RLM was expressed uniquely in hepatocytes while there was no expression in other cells such as the simple cuboidal or columnar epithelium

EXAMPLE 3

Signaling Potential of STAT 5 Activation by IL-17RLM

Figure 3A:
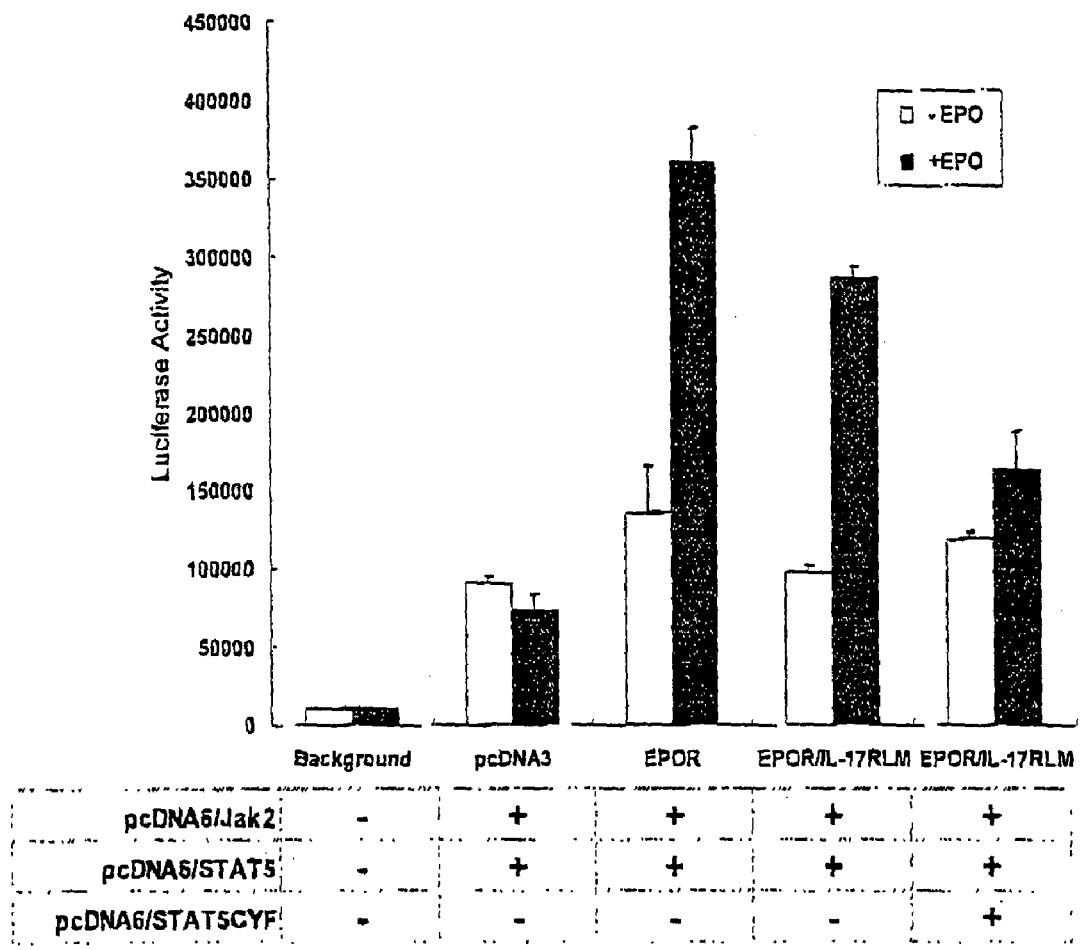
Figure 3B:
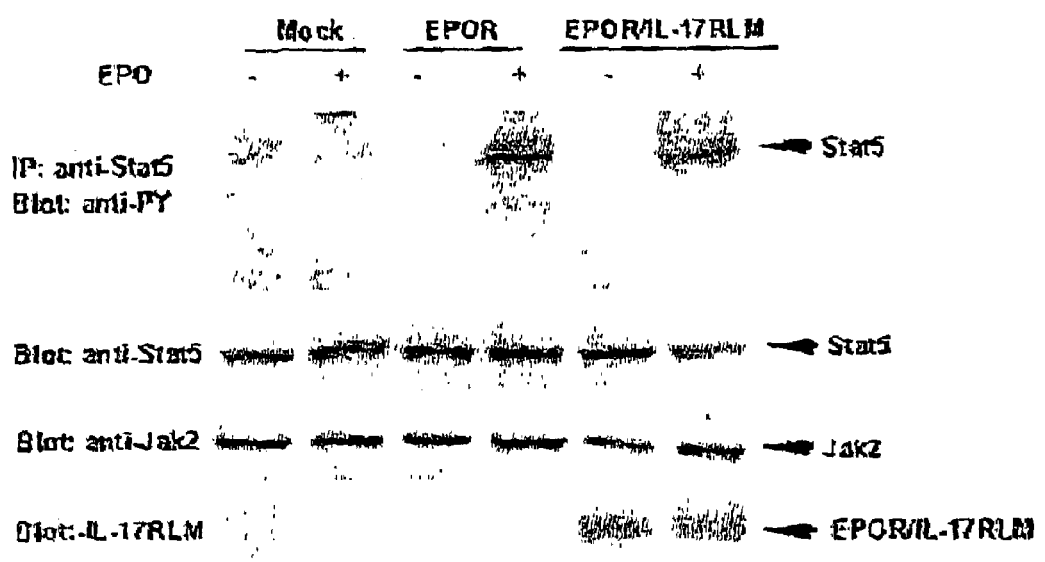

It is noteworthy that IL-17RLM contains a SH3 interaction domain and many potential tyrosine phosphorylated sites in the intracellular domain of his protein. We reasoned that IL-17RLM might signal the STAT pathway. To test this hypothesis, we constructed a chimeric molecule fusing the extracellular and transmembrane domains of erythropoietin receptor with the intracellular domain of IL-17RLM. We carried out luciferase assay using a STAT5-responsive luciferase reporter plasmid transfected into COS7 cells. As shown in FIG. 3A, this chimeric receptor (EPOR/hIL-17RLM) mediated STAT5 activation significantly upon EPO stimulation. Moreover, STAT5 CYF, a dominant mutant of STAT5, could inhibit STAT5 activation, suggesting that the chimeric receptor specifically activated STAT5.

Next we evaluated whether the chineric molecule (EPOR/hIL-17RLM) could mediate STAT5 tyrosine phosphorylation in response to EPO. STAT5 was immunoprecipitated with anti-STAT5 antibody and blotted with anti-phosphotyrosine (anti-PY). The results showed that both the EPOR and EPOR/hIL-17RLM could mediate STAT5 tyrosine phosphorylation in the presence of EPO (FIG. 3B, up panel) while the equal amounts of STAT5 or JAK protein were expressed (FIG. 3B, middle panels), suggesting that IL-17RLM may signal through initiation of STAT5 tyrosine phosphorylation.

Figure 3C:
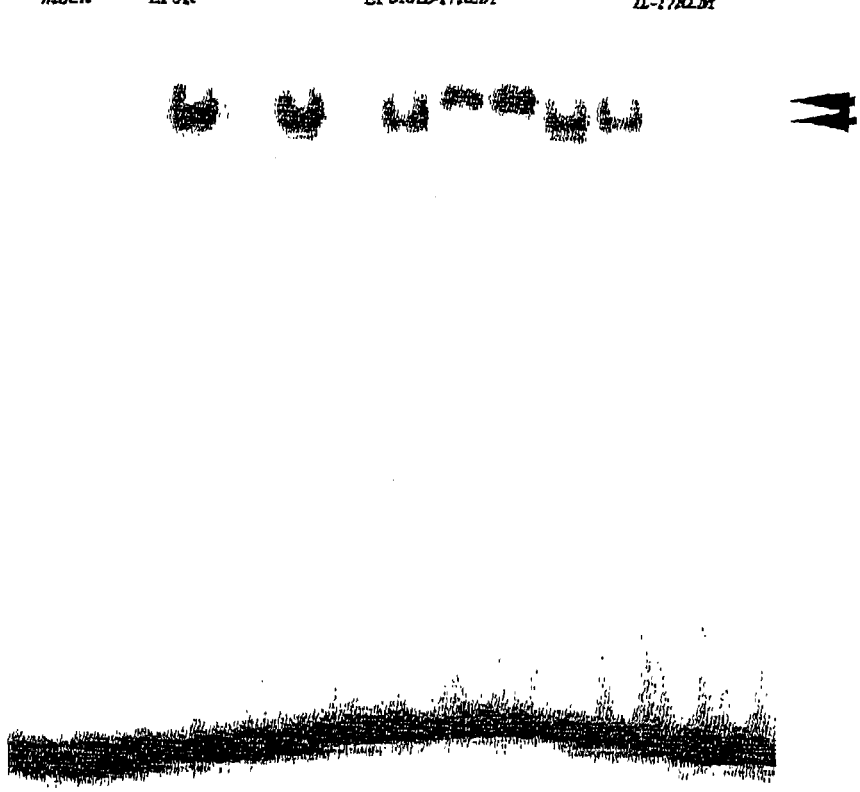

We further performed electrophoretic mobility-shift assay to investigate whether EPOR/hIL-17RLM chimeric receptor could increase STAT5 DNA-binding activity upon the stimulation of EPO. As shown in FIG. 3C, both EPOR and EPOR/IL-17RLM stimulated STAT5 binding strongly to DNA in the presence of EPO (FIG. 3C, lanes 4 and 6). The specificity was confirmed by adding cold probes as competitors (FIG. 3C, lanes 7 and 8) or by adding anit-STAT5 antibody for supershift (FIG. 3C, lanes 9 and 10). As is known that STAT5 might form homo-dimer or heter-dimer with other STATs, we tested the shift band by adding anti-STAT1 (FIG. 3C, lane 11) or anti-STAT3 (FIG. 3C, lane 12) antibody. The results showed that none of the anti-STAT1 or anti-STAT3 antibody could drive the band to supershift, suggesting that EPOR/IL-17RLM stimulated STAT5 homodimerization The specificity for the STAT5 activation was further confirmed by the overexpression of STAT5 CYF, which blocked STAT5 activation (FIG. 3C, lanes 15 and 16)

To detect the signal potential of the endogenous STAT5 activation mediated by EPOR/hIL-17RLM chimeric receptor, the EPOR/hIL-17RLM or EPOR was stably transfected into Ba/F3 cells and the gel shift assays were performed. The results showed that STAT5 was activated in a time course in the presence of EPO (FIG. 3D). Importantly, when we detected the activation of endogenous STAT5, we found that EPOR/hIL-17RLM was more likely to stimulate STAT5b rather than STAT5a (FIG. 3E, lanes 9, 10 and 11). Altogether, these data suggested that the novel receptor could mediate STAT5 signal pathway.

EXAMPLE 4

Chimeric hIL-17RLM Promotes Cell Proliferation in BA/F3 Cells

To address whether IL-17RLM was capable of transmitting a proliferation signal, we set up Ba/F3/EPOR and Ba/F3/EPOR/hIL-17RLM stably expressed cell lines. We carried out the cell proliferation assay using those cells. As shown in FIG. 4A, the Ba/F3 cells had no proliferative response to EPO, while the Ba/F3/EPOR cells had strong proliferative response. Interestingly, the Ba/F3/EPOR/hIL-17RLM cells had also a significant proliferative response to EPO in a dose dependent manner (FIG. 4A) and a time course of manner (FIG. 4B). Moreover, the Ba/F3/EPOR/hIL-17RLM cells could be maintained for a longer time in presence of low dose of EPO (data not shown). These results suggested that IL-17RLM could be a novel signaling receptor that could signal Ba/F3 cell proliferation. Based on the result that EPOR/hIL-17RLM specifically activated STAT5, we reasoned that EPOR/d-17RLM stimulated Ba/F3 cell proliferation possibly through the activation of STAT5 pathway.

EXAMPLE 5

IL-17RLM Interacted with FGFR

It has been reported that FGFRs were highly expressed in kidney tissue (36), where hIL-17RLM was abundant also (FIGS. 2A and E). Based on the fact that mSef interacted with FGFRs (28), we reasoned that hIL-17RLM could also interact with FGFRs and affect FGF signaling. To detect whether the physical interaction of the two receptors occurred, we carried out co-immunoprecipitation assay by co-expression of the two proteins in Cos7 cells. We successfully precipitated the FGFR1 (FIG. 5A) and FGFR2 (FIG. 5B) using anti-IL-17RLM serum but failed to precipitate FGFR3 (data not shown), suggesting that IL-17RLM specifically interacted with FGFR1 and FGFR2 in the intact cells. These results were consistent with the report about the interaction of zebrafish zSef with xenopus FGFR1 or FGFR2 (28). It also implied that hIL-17RLM might elicit a similar effect on FGFR signaling to Spred or Sprouty family members, which inhibited FGFR signaling strongly (37–40).

Figure 5A:
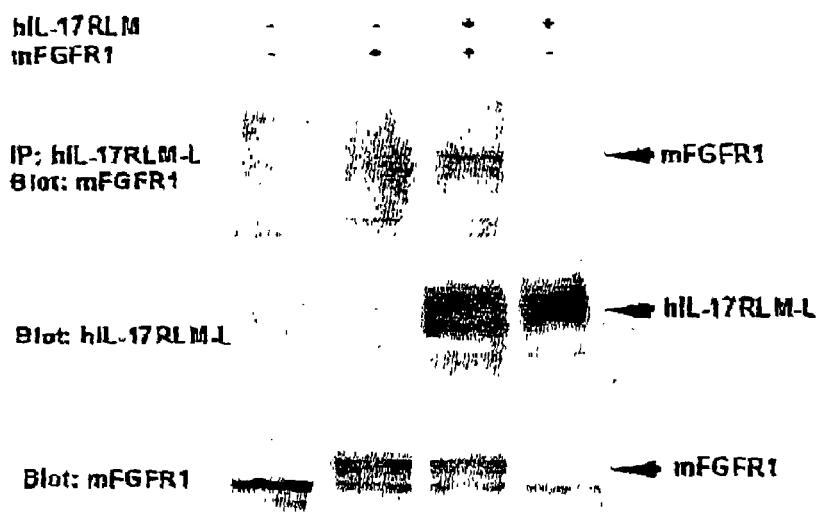
Figure 5B:
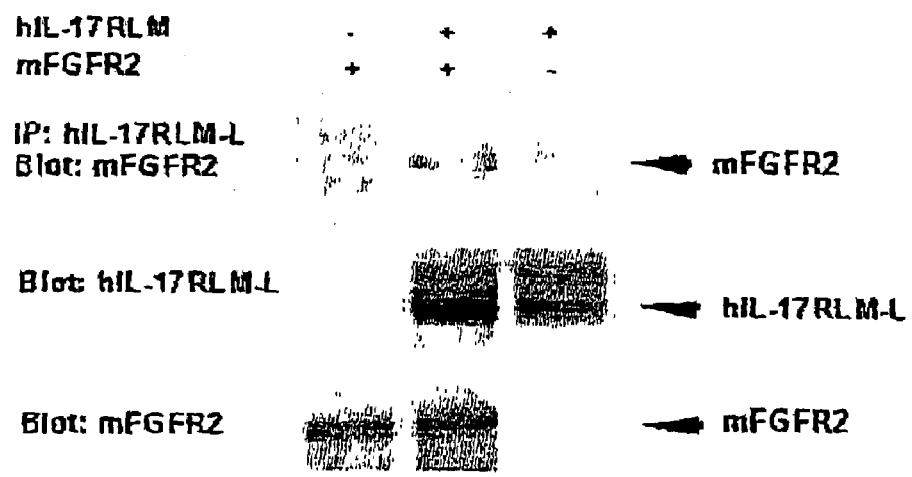
Figure 5C:
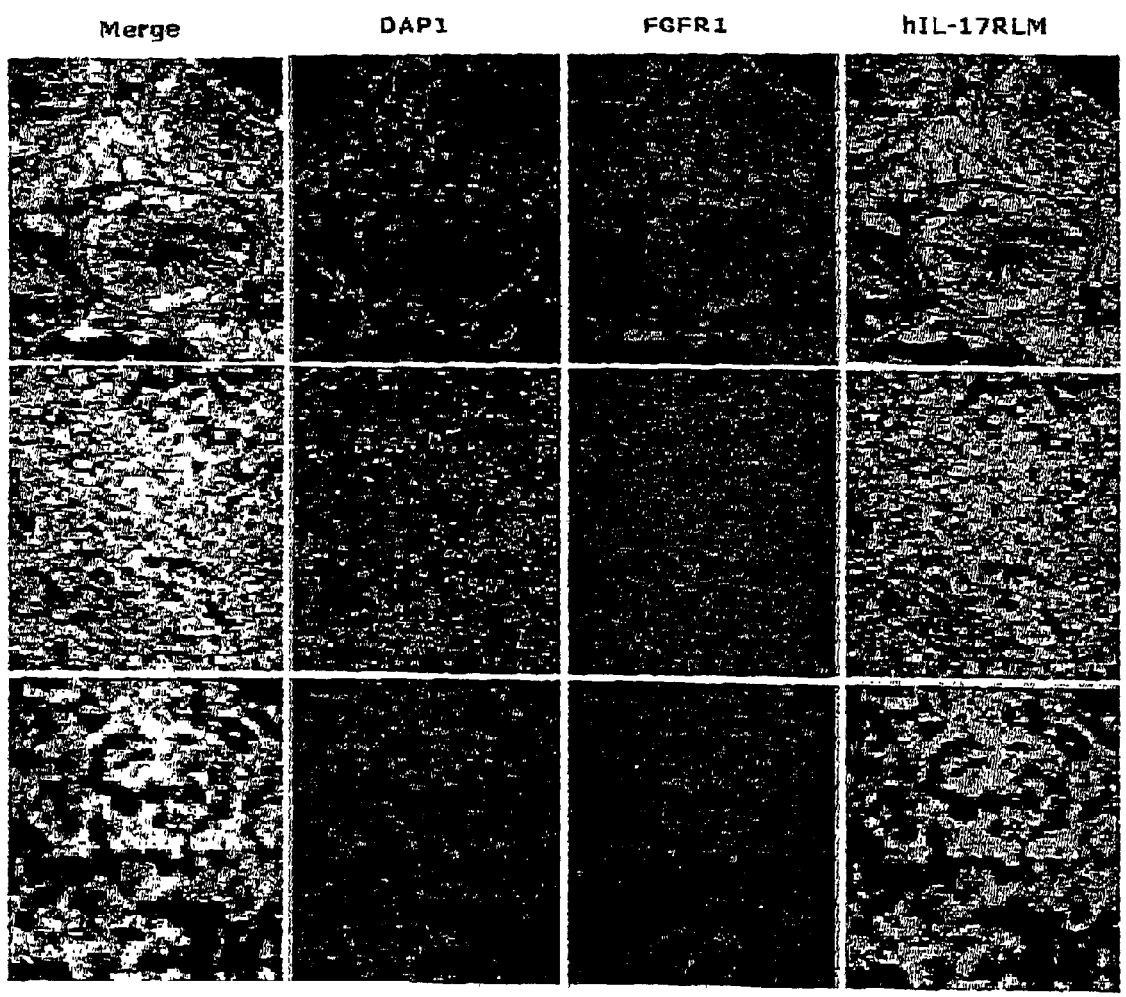
Figure 5D:

To furthermore examine whether the co-expression of the two receptors occurred in human tissue, we carried out the immunostaining assay with the anti-FGFR1 antibody and anti-hIL-17RLM serum. The results demonstrated that hIL-17RLM was co-expressed with FGFR1 in kidney (FIG. 5C), suggesting that hIL-17RLM co-localized with FGFR1 in normal human tissue. Interestingly, when we over-expressed both hIL-17RLM and FGMR2, we found the complete co-localization of the two proteins (FIG. 5D). Taken together, these data suggested that hIL-17RLM interacted with FGFR1 and FGFR2 but not FGFR3.

Figure 6B:
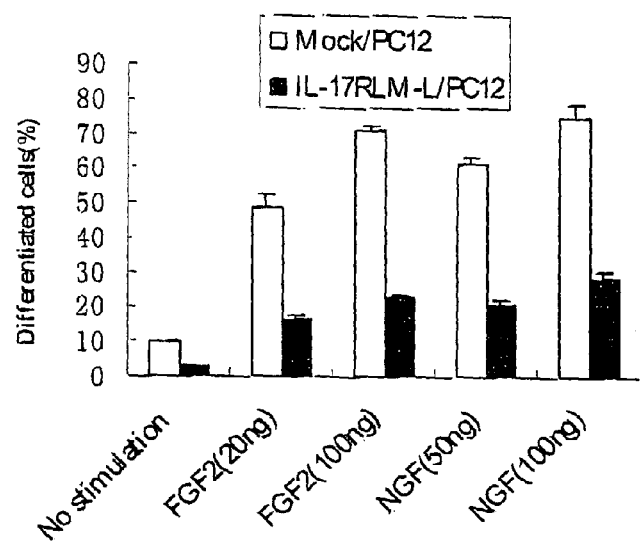
Figure 6C:
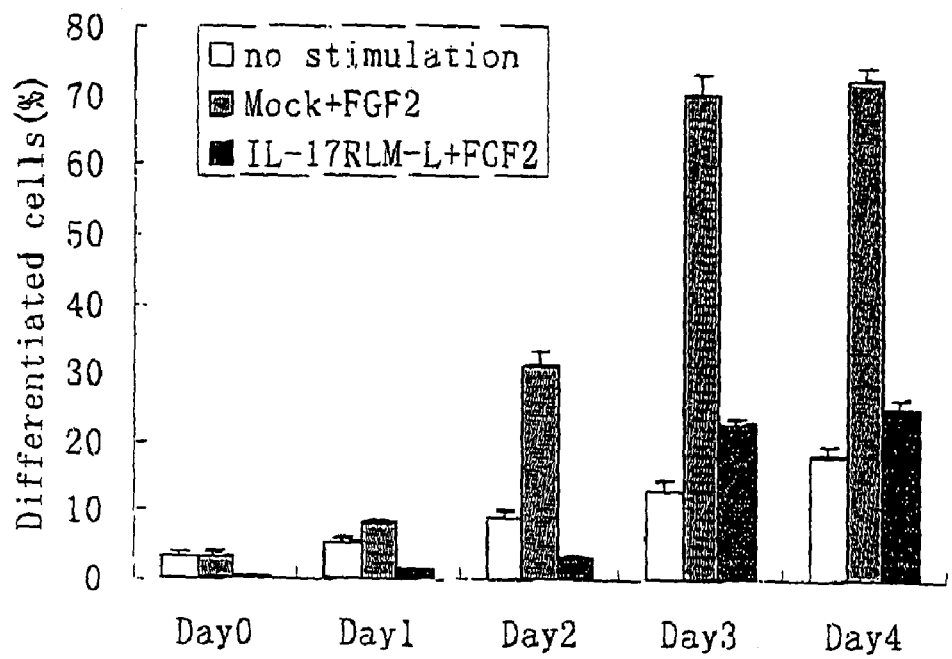
Figure 6D:
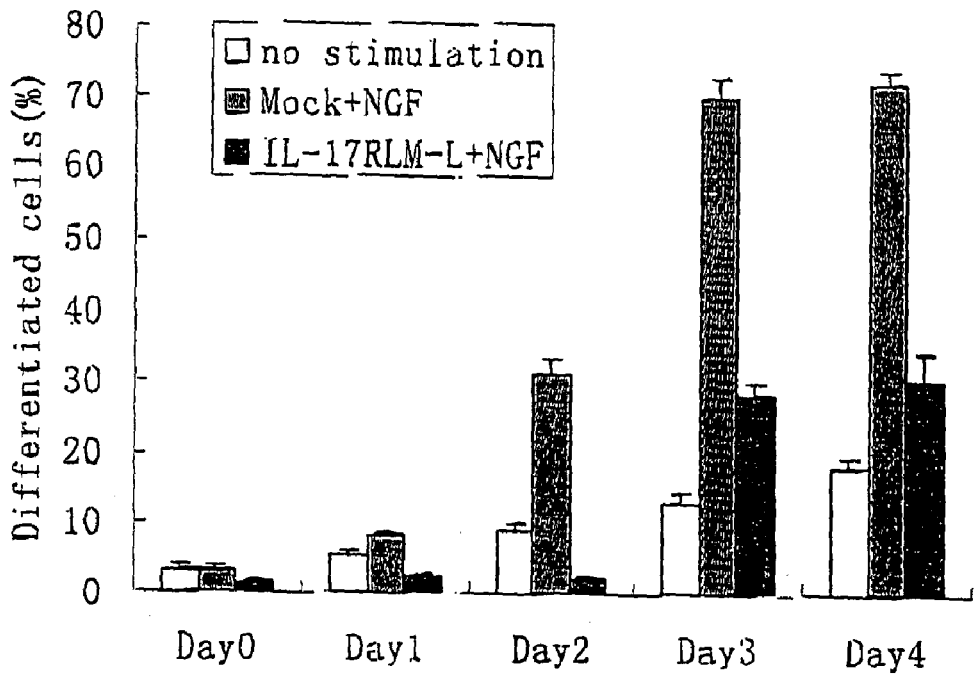

EXAMPLE 6 hIL-17RLM-L strongly inhibits basic FGF2 or NGF-induced PC12 cell differentiation Based on the observation that hIL-17RLM was able to interact with FGFR1 and FGFR2, we examined whether hIL-17RLM could affect FGF signaling. We stably expressed hIL-17RLM-L in PC12 cells, a rat pheochromocytoma cell line which could be induced into sympathetic neuron-like cells possessing elongated neuritis by basic fibroblast growth factor (FGF-2) or NGF. The data showed that hIL-17RLM elicited strong inhibitory effects on the differentiation of PC12 cells (FIG. 6A). When the differentiated cell numbers were calculated, it was obvious that the inhibitory effects of hIL-17RLM on the differentiation could be sustained even when the cells were exposed to higher dose of FGF2 or NGF (FIGS. 6A, and 6B). When the cells were exposed to FGF2 or NGF for a longer time, it was still significant that hIL-17RLM inhibited the PC12 cell differentiation (FIGS. 6C and 6D). All the results indicated hIL-17RLM could significantly inhibit the differentiation of PC12 cells stimulated by FGF2 or NGF, even in the condition of higher dose or prolonged exposure.

Figure 6F:
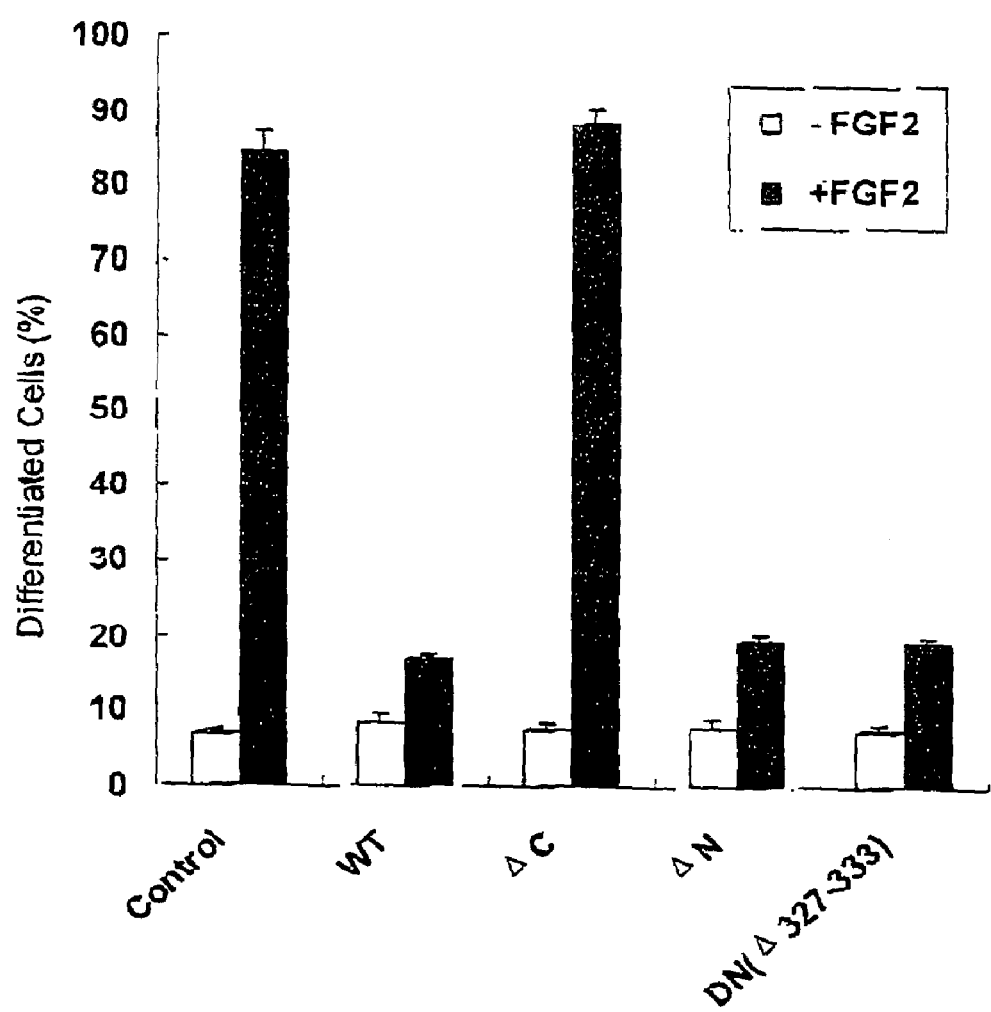

To further determine which domain of hIL-17RLM was necessary for the inhibition of PC12 cell differentiation induced by FGF2, we constructed the N-terminal truncated mutant hIL-7RLM-L(ΔN), which lacks N-terminal extracellular domain of hIL-17RLM, the C-terminal truncated mutant hIL-17RLM-17 L(ΔC), which lacks C-terminal intracellular domain of hIL-17RLM, and a mutant hIL-7RLM-L(DN), which lacks a motif (E327-L333) in the intracellular domain containing a putative tyrosine phosphorylation site. We overexpressed these mutants with EGFP in PC12 cells in the presence or absence of FGF. The results showed that overexpression of hIL-17RLM-L(ΔN) or hIL-17RLM4-L(DN) had similar inhibitory effects on FGF2-induced PC12 cell differentiation, as in the case of hIL-17RLM-L(WT) (FIGS. 6E and 6F). However, overexpression of hIL-17RLM-L(ΔC) had no inhibitory effects on the differentiation of PC12 cells, suggesting that the intracellular domain played a critical role in the inhibition of PC12 cell differentiation induced by FGF2. The results also suggested hIL-17RLM-L(DN), which lacks a motif (E327~L333) in the intracellular domain of hIL-17RLM-L, may not function as a dominant negative form.

EXAMPLE 7 hIL-17RLM Inhibited Ras-MAPK Signaling Pathway

Figure 7A:
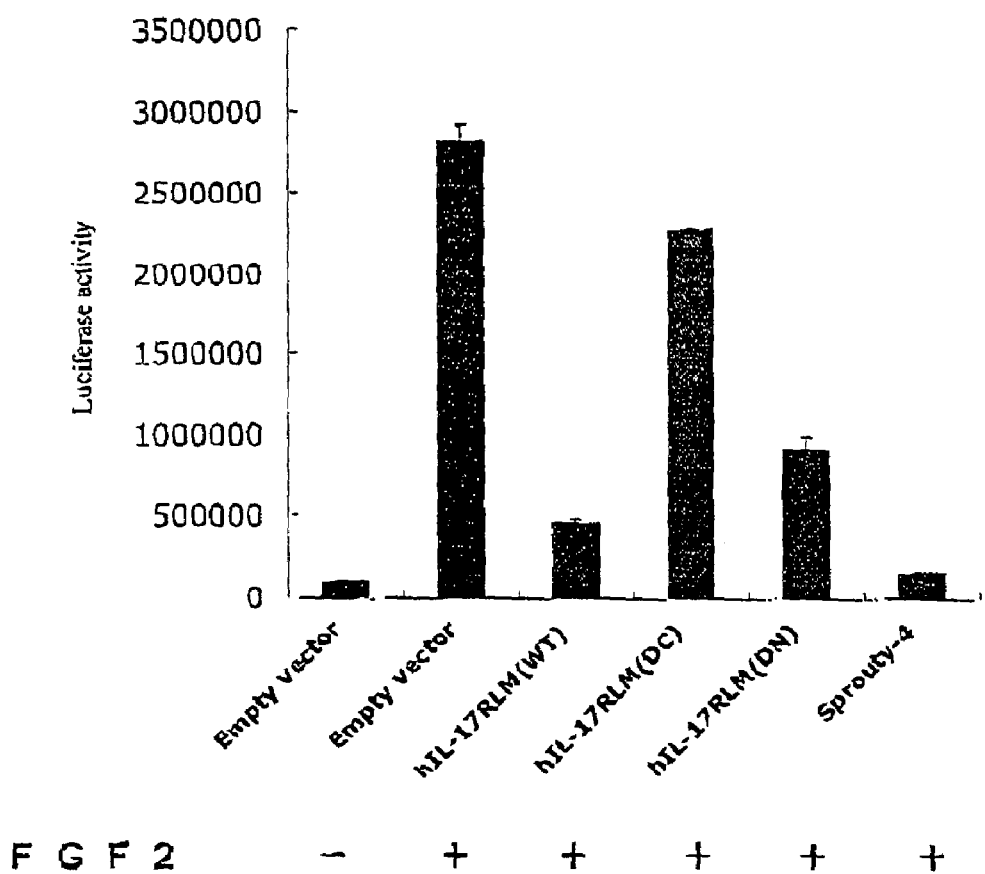
Figure 7B:
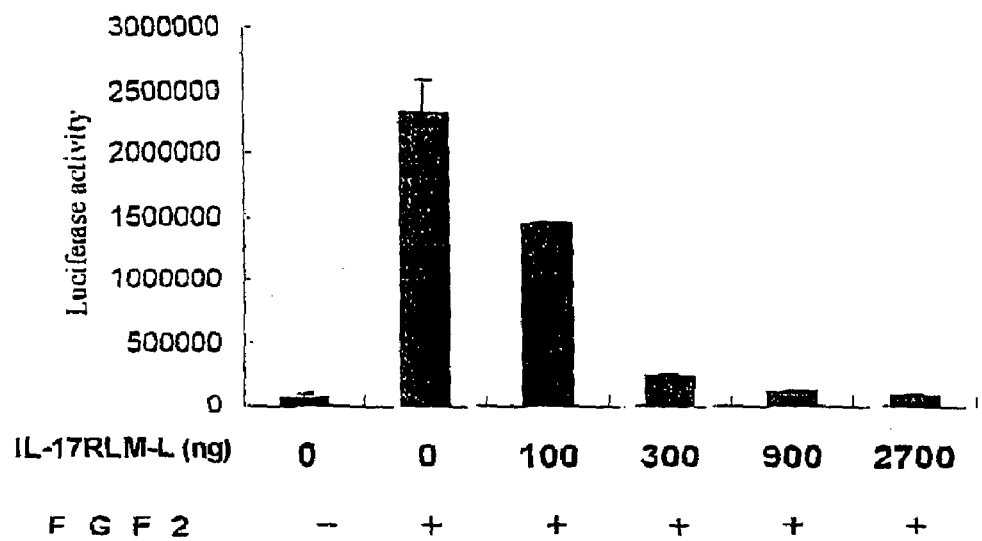
Figure 7C:
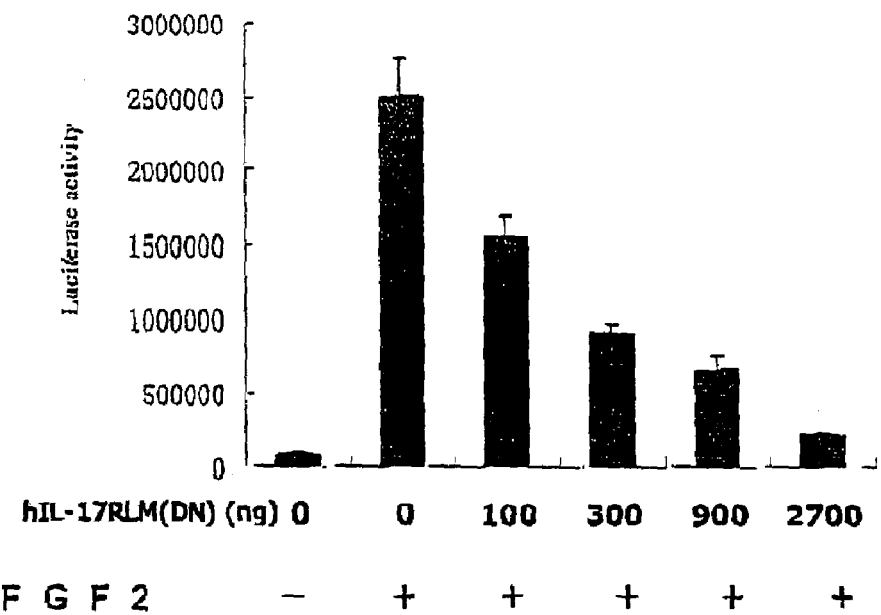

It has been reported Ras-MAPK signaling was required for FGF2-induced PC12 cell differentiation. To investigate the role of hIL -17RLM in MAPK activation during FGF2-induced PC12 cell differentiation, we detected the effects of IL-17RLM on Elk-1 mediated luciferase activity. The data showed that overexpression of hIL-17RLM significantly suppressed FGF2-induced Elk-1 luciferase activity in PC12 cells (FIG. 7A), which is comparable to the role of Sprouty 4 (37–39). Compared with IL-17RLM-L, the C-terminal truncated mutant hIL-17RLM-L(ΔC) and the N-terminal truncated mutant hIL-17RLM-L(ΔN) had about 23% and 81% of the inhibitory effect, respectively (FIG. 7 A column 4,5). The result was also correlated with the inhibitory effect of hTL-17RLM on the FGF2-induced PC12 cell differentiation. Furthermore, our results showed both hIL-17RLM-L(WT) and hIL-17RLM-L(ΔN) suppressed FGF2dependent Elk-1 luciferase activity in PC 12 cells in a dose-dependent manner (FIGS. 7B and 7C).

Figure 7D:
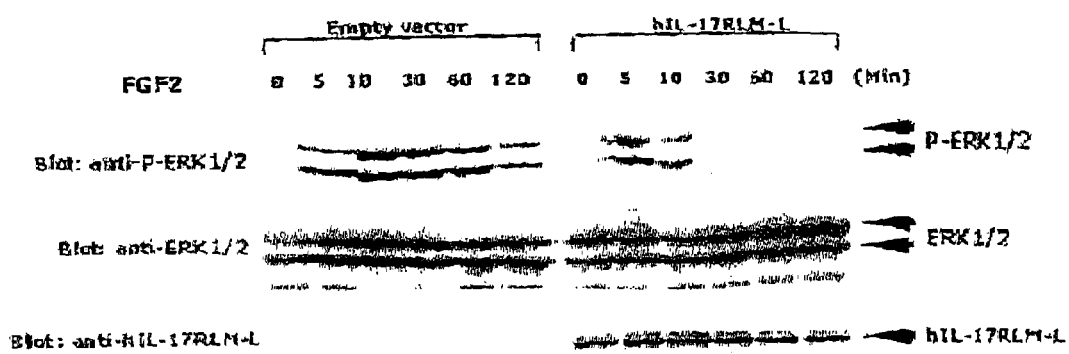
Figure 7E:
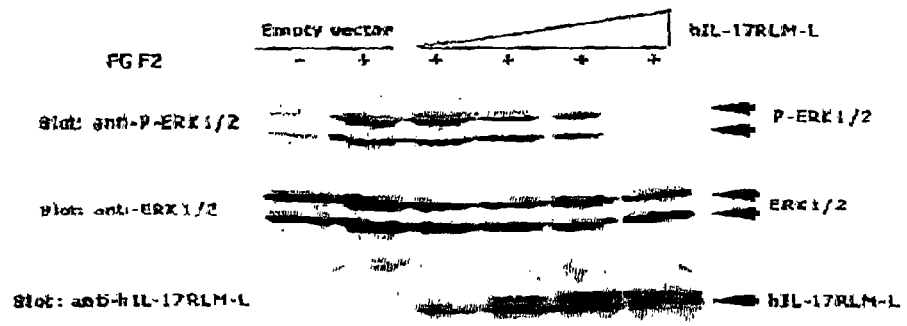

Earlier studies showed that activation of ERK1/2 was important for neurite outgrowth in PC12 cells, and ERK1/2 phosphorylation was strongly but transiently induced by FGF2, with the level of phosphorylation reaching a maximum within 5–10 minutes and then declining to lower sustained levels. With this in mind, we examined whether hIL-17RLM-L suppressed endogenous ERK1/2 activation induced by FGF2 in PC12 cells. As shown in FIG. 7D, overexpression of hIL-17RLM-L significantly suppressed the endogenous ERK phosphorylation, with the maximum inhibition at 10 min after stimulation. Additionally, hIL-17RLM exhibited an inhibitory effect on ERK activation in a dose dependent manner (FIG. 7E). These results indicated that hIL-17RLM could inhibit FGF2-induced PC12 cell differentiation possibly through the inhibition of Ras-MAPK signaling

Figure 8A:
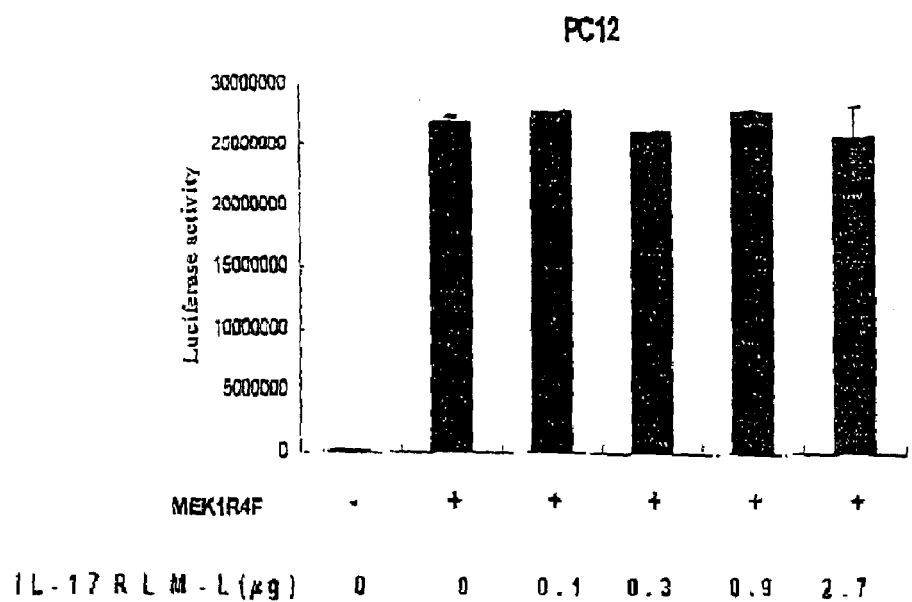
Figure 8B:
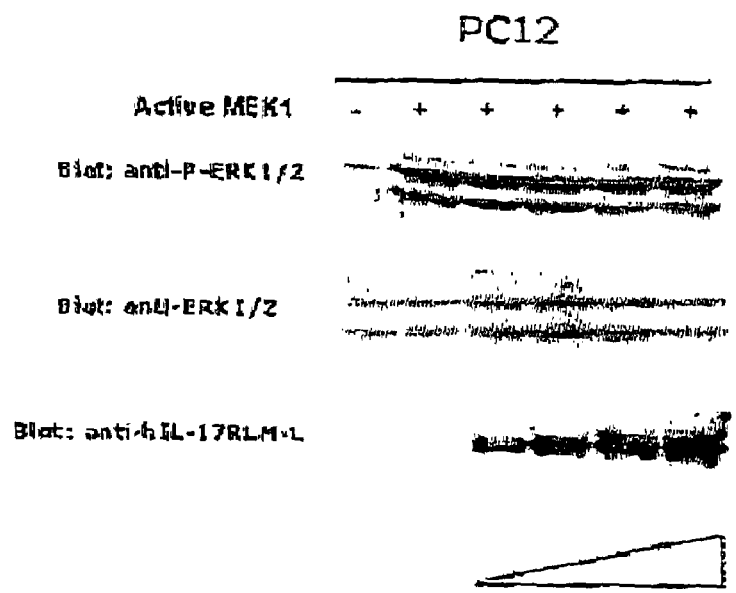
Figure 8C:
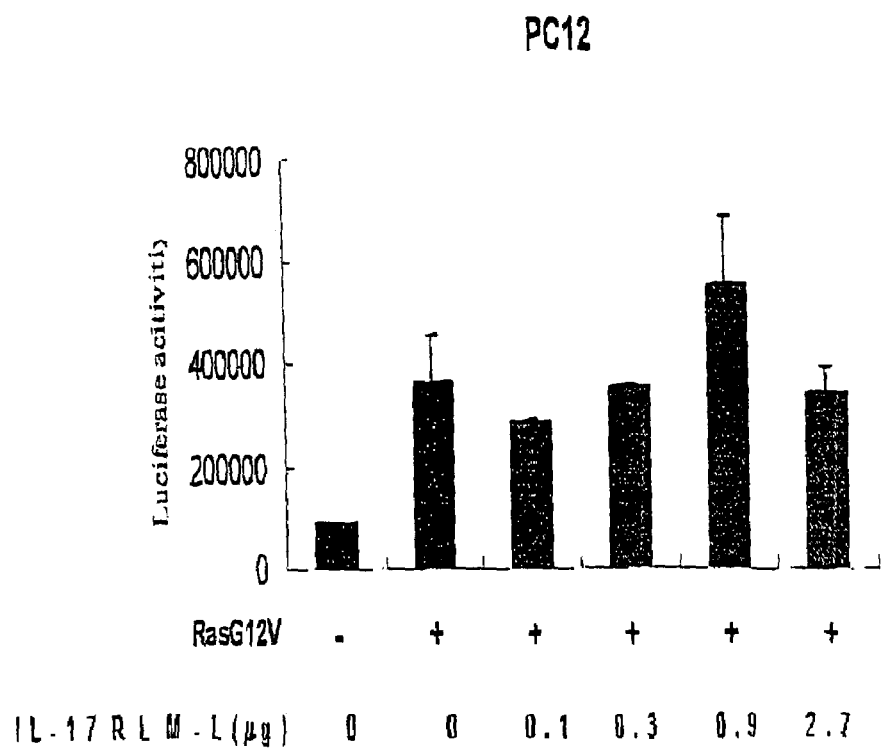
Figure 8D:
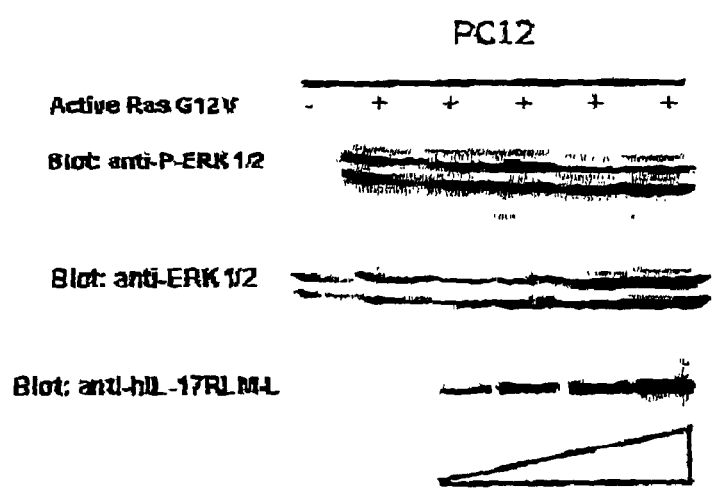
Figure 9:
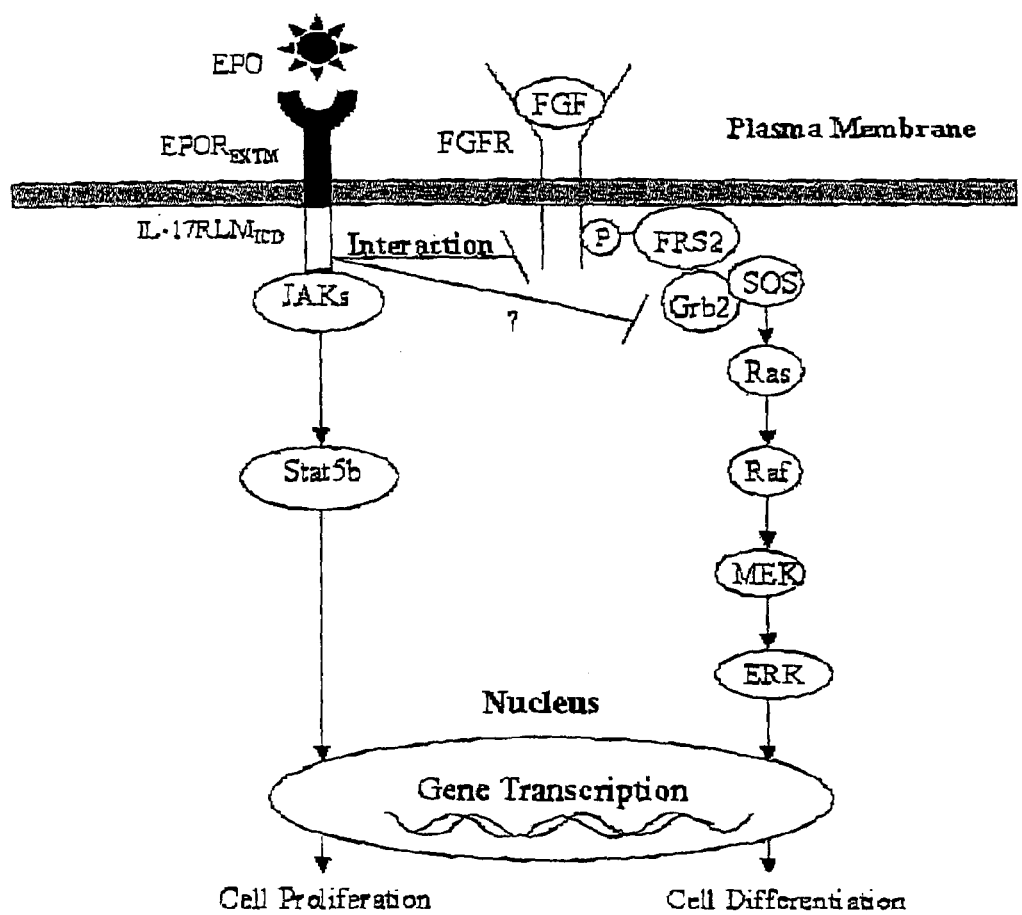

EXAMPLE 8 hIL-17RLM Inhibited Ras-MAPK Signaling Pathway by Acting on the Up-Stream Signal Molecule of Ras Next, we investigated which signaling component of Ras-MAPK pathway was suppressed by IL-17RLM. We recruited constitutively active Ras (G12V) or active MEK (MEK1RF) to check the activation of ERK by luciferase assay or Western botting in PC12 cells. Both the luciferase assay and Western blotting analysis showed that hIL-17RLM had no effect on the signaling pathway mediated by constitutively active Ras (FIGS. 8A and B) and MEK (FIGS. 8C and D). These data were repeated in 293T cells (data not shown), suggesting that the target of IL-17RLM was probably located on the upstream signaling molecules of Ras in FGFR-Ras-MAPK signaling pathway.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosure of all applications, patents and publications, cited herein and of corresponding Chinese application No. 02123447.7, filed Jun. 28, 2002, is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

REFERENCES

1. Yao, Z., Fanslow, W. C., Seldin, M. F., Rousseau, A. M., Painter, S. L., Comeau, M. R., Cohen, J. I., and Spriggs, M. K. (1995) Herpesvirus Saimiri encodes a new cytokine, IL-17, which binds to a novel cytokine receptor. *Immunity* 3, 811–821
2. Yao, Z., Painter, S. L., Fanslow, W. C., Ulrich, D., Macduff, B. M., Spriggs, M. K., and Armitage, R. J. (1995) Human IL-17: a novel cytokine derived from T cells. *J Immunol* 155, 5483–5486
3. Yao, Z., Spriggs, M. K., Derry, J. M., Strockbine, L., Park, L. S., VandenBos, T., Zappone, J. D., Painter, S. L., and Armitage, R. J. (1997) Molecular characterization of the human interleukin (IL)-17 receptor. *Cytokine* 9, 794–800
4. Spriggs, M. K. (1997) Interleukin-17 and its receptor. *J Clin Immunol* 17, 366–369
5. Fujino, S., Andoh, A., Bamba, S., Ogawa, A., Hata, K., Araki, Y, Bamba, T., and Fujiyama, Y. (2003) Increased expression of interleukin 17 in inflammatory bowel disease. *Gut* 52, 65–70
6. Li, H., Chen, J., Huang, A., Stinson, J., Heldens, S., Foster, J., Dowd, P., Gurney, A. L., and Wood, W. I. (2000) Cloning and characterization of IL-17B and IL-17C, two new members of the IL-17 cytokine family. *Proc Natl Acad Sci USA* 97, 773–778
7. Moore, E. E., Presnell, S., Garrigues, U., Guilbot, A., LeGvern, E., Smith, D., Yao, L., Whitmore, T. E., Gilbert, T., Palmer, T. D., Homer, P. J., and Kauester, R. E. (2002) Expression of IL-17B in neurons and evaluation of its possible role in the chromosome 5q-linked form of Charcot-Marie-Tooth disease. *Neeuromuscul Disord* 12, 141–150
8. Shi, Y., Ulrich, S. I., Zhang, J., Connolly, K., Grzegorzewski, K. J., Barber, M. C., Wang, W., Wathen, K., Hodge, V, Fisher, C. L., Olsen, H., Ruben, S. M., Knyazev, I., Cho, Y. H., Kao, V., Wilkinson, K. A., Carrell, J. A., and Ebner, R. (2000) A novel cytokine receptor-ligand pair. Identification, molecular characterization, and in vivo immunomodulatory activity. *J Biol Chem* 275, 19167–19176
9. Lee, J., Ho, W. H., Maruoka, M., Corpuz, R. T., Baldwin, D. T., Foster, J. S., Goddard, A. D., Yansura, D. G., Vandlen, R. L., Wood, W. I., and Gurney, A. L. (2001) IL17E, a novel proinflammatory ligand for the IL-17 receptor homolog IL-17Rh1. *J Biol Chem* 276, 1660–1664
10. Pan, (a, French, D., Mao, W., Marvoka, M., Risser, P., Lee, J., Foster, J., Aggarwal, S., Nicholes, K., Guillet, S., Schow, P., and Gurney, A. L. (2001) Forced expression of murine IL-17E induces growth retardation, jaundice, a Th2-biased response, and multiorgan inflammation in mice. *J Immunol* 167, 6559–6567

11. Stames, T., Robertson, M, J., Sledge, G., Kelich, S., Nakshatri, H., Broxmeyer, H. E., and Hromas, R. (2001) Cutting edge: IL-17F, a novel cytokine selectively expressed in activated T cells and monocytes, regulates angiogenesis and endothelial cell cytokine production. *J Immunol* 167, 4137–4140

12. Hymowitz, S. G, Filvaroff, E. H., Yin, J. P., Lee, J., Cai, L., Risser, P., Maruoka, M., Mao, W., Foster, J., Kelley, R. F., Pan, G., Gurney, A. L., de Vos, A. M., and Starovasnik, M. A. (2001) IL-17s adopt a cystine knot fold: structure and activity of a novel cytokine, IL-17F, and implications for receptor binding. *Embo J* 20, 5332–5341

13. Fort, M. M., Cheung, J., Yen, D., Li, J., Zurawski, S. M., Lo, S., Menon, S., Clifford, T., Hunte, B., Lesley, R., Muchamuel, T., Hurst, S. D., Zurawski, G., Leach, M. W., Gorman, D. M., and Rennick, D. M. (2001) IL-25 induces IL4, IL-5, and IL-13 and Th2-associated pathologies in vivo. *Immunity* 15, 985–995

14. Haudenschild, D., Moseley, T., Rose, L., and Reddi, A. H. (2002) Soluble and transmembrane isoforms of novel interleukin-17 receptor-like protein by RNA splicing and expression in prostate cancer. *J Biol Chem* 277, 4309–4316

15. Shalom-Barak, T., Quach, J., and Lotz, M. (1998) Interleukin-17-induced gene expression in articular chondrocytes is associated with activation of mitogen-activated protein kinases and NF-kappaB. *J Biol Chem* 273, 27467–27473

16. Awane, M., Andres, P. G., Li, D. J., and Reinecker, H. C. (1999) NF-kappa B-inducing kinase is a common mediator of IL-17-, TNF-alpha-, and IL-1 beta-induced chemokine promoter activation in intestinal epithelial cells. *J Immunol* 162, 5337–5344

17. Martel-Pelletier, J., Mineau, F., Jovanovic, D., Di Battista, J. A., and Pelletier, J. P. (1999) Mitogen-activated protein kinase and nuclear factor kappaB together regulate interleukin-17-induced nitric oxide production in human osteoarthritic chondrocytes: possible role of transactivating factor mitogen-activated protein Kinase-activated proten kinase (MAPKAPK). *Arthritis Rheum* 42, 2399–2409

18. Shimada, M., Andoh, A., Hata, K., Tasaki, K., Araki, Y, Fujiyama, Y., and Bamba, T. (2002) IL-6 secretion by human pancreatic periacinar myofibroblasts in response to inflammatory mediators. *J Immunol* 168, 861–868

19. Subramaniam, S. V., Pearson, L. L., and Adunyah, S. E. (1999) Interleukin-17 induces rapid tyrosine phosphorylation and activation of raf-1 kinase in human monocytic progenitor cell line U937. *Biochem Biophys Res Commun* 259, 172–177

20. Subramaniam, S. V., Cooper, R. S., and Adunyah, S. E. (1999) Evidence for the involvement of JAK/STAT pathway in the signaling mechanism of interleukin-17. *Biochem Biophys Res Commun* 262, 14–19

21. Schwandner, R., Yamaguchi, K., and Cao, Z. (2000) Requirement of tumor necrosis factor receptor-associated factor (TRAF)6 in interleukin 17 signal transduction. *J Exp Med* 191, 1233–1240

22. O'Neill, L. A. (2000) The interleukin-1 receptor/Toll-like receptor superfamily: signal transduction during inflammation and host defense. *Sci STKE* 2000, RE1

23. Akira, S., Takeda, K., and Kaisho, T. (2001) Toll-like receptors: critical proteins linking innate and acquired immunity. *Nat Immunol* 2, 675–680

24. Daun, J. M. and Fenton, M. J. (2000) Interleukin-1/Toll receptor family members: receptor structure and signal transduction pathways. *J Interferon Cytokine Res* 20, 843–855

25. O'Neill, L. (2000) The Toll/interleukin-1 receptor domain: a molecular switch for inflammation and host defence. *Biochem Soc Trans* 28, 557–563

26. Bowie, A., and O'Neill, L. A. (2000) The interleukin-1 receptor/Toll-like receptor superfamily: signal generators for pro-inflammatory interleukins and microbial products. *J Leukoc Biol* 67, 508–514

27. Furthauer, M., Lin, W., Ang, S. L., Thisse, B., and Thisse, C. (2002) Sef is a feedback-induced antagonist of Ras/MAPK-mediated FGF signalling. *Nat Cell Biol* 4, 170–174

28. Tsang, M., Friesel, R., Kudoh, T., and Dawid, I. B. (2002) Identification of Sef, a novel modulator of FGF signalling. *Nat Cell Biol* 4, 165–169

29. Kovalenko, D., Yang, X., Nadeau, R. J., Harkins, L. K., and Friesel, R. (2003) Sef inhibits fibroblast growth factor signaling by inhibiting FGFR1 tyrosine phosphorylation and subsequent ERK activation. *J Biol Chem*

30. Burge, C., and Karlin, S. (1997) Prediction of complete gene structures in human genomic DNA. *J Mol Biol* 268, 78–94

31. Nielsen, H., Brunaak, S., and von Heijne, G (1999) Machine learning approaches for the prediction of signal peptides and other protein sorting signals. *Protein Eng* 12, 3–9

32. Landolt-Marticorena, C., Williams, K. A., Deber, C. M., and Reithmcier, R. A. (1993) Non-random distribution of amino acids in the trauraembrane segments of human type I single span membrane proteins. *J Mol Biol* 229, 602–608

33. Bazan, J. F. (1990) Structural design and molecular evolution of a cytokine receptor superfamily. *Proc Natl Acad Sci USA* 87, 6934–6938

34. Murakami, M., Narazaki, M.Mibi, M., Yawata, H., Yasukawa, K., Hamaguchi, M., Taga, T., and Kishimoto, T. (1991) Critical cytoplasmic region of the interleulin 6 signal transducer gp130 is conserved in the cytokine receptor family. *Proc Natl Acad Sci USA* 88, 11349–11353

35. Ye, H., Arron, J. R., Lamothe, B., Cirilli, M., Kobayashi, T. Shevde, N. K., Segal. D., Dzivenu, O. K., Vologodskaia, M., Yim, M., Du, K., Singn, S., Pike, J. W., Darnay, B. G., Choi, Y., and Wu, H. (2002) Distinct molecular mechanism for initiating TRAF6 signalling. *Nature* 418, 443–447

36. Cancilla, B., Davies, A., Cauchi, J. A., Risbridger, G. P., and Bertram, J. F. (2001) Fibroblast growth factor receptors and their ligands in the adult rat kidney. *Kidney Int* 60, 147–155

37. Wakioka, T., Sasaki, A., Kato, R., Shouda, T., Matsumoto, A., Miyoshi, K., Tsuneoka, M., Koriya, S., Baron, R., and Yoshimura, A. (2001) Spred is a Sprouty-related suppressor of Ras signalling. *Nature* 412, 647–651

38. Yusoff, P., Lao, D. H., Ong, S. H., Wong, E. S., Lim, J., Lo, T. L., Leong, H. F., Fong, C. W., and Guy, G. R. (2002) Sprouty2 inhibits the Ras/MAP kinase pathway by inhibiting the activation of Raf. *J Biol Chem* 277, 3195–3201

39. Casci, T., Vinos, J., and Freeman, M. (1999) Sprouty, an intracellular inhibitor of Ras signaling. *Cell* 96, 655–665

40. Hacohen, N., Kramer, S., Sutherland, D., Hiromi, Y., and Krasnow, M. A. (1998) sprouty encodes anovel antagonist of FGF signaling that patterns apical branching of the *Drosophila* airways. *Cell* 92, 253–263
41. Moseley, T. A., Haudenschild, D. R., Rose, L., and Reddi, A. H. (2003) Interleukin-17 family and IL-17 receptors. *Cytokine Growth Factor Rev* 14, 155–174
42. Anderson, K. V. (2000) Toll signaling pathways in the innate immune response. *Curr Opin Immunol* 12, 13–19
43. Lemaitre, B., Nicolas, E., Michaut, L., Reichhart, J. M., and Hoffmann, J. A. (1996) The dorsoventral regulatory gene cassette spatzle/Toll/cactus controls the potent antifungal response in Drosophila adults. *Cell* 86, 973–983
44. Dreijerink, K., Braga, E., Kuzmin, I., Geil, L., Duh, F. M., Angeloni, D., Zbar, B., Lerman, M. I., Stanbridge, E. J., Minna, J. D., Protopopov, A., Li, J., Kashuba, V., Klein, G., and Zabarovsky, E. R. (2001) The candidate tumor suppressor gene, RASSF1A, from human chromosome 3p21.3 is involved in kidney tumorigenesis. *Proc Natl Acad Sci USA* 98, 7504–7509
45. Alimov, A., Kost-Alimova, M., Liu, J., Li, C., Bergerheim, U., Imreh, S., Klein, G., and Zabarovsky, E. R. (2000) Combined LOH/CGH analysis proves the existence of interstitial 3p deletions in renal cell carcinoma *Oncogene* 19, 1392–1399
46. Shi, G., Web, H. J., Martensen, S., Seeger, D., and Hossfeld, D. K. (1996) 3p21 is a recurrent treatment-related breakpoint in myelodysplastic syndrome and acute myeloid leukemia. *Cytogenet Cell Genet* 74, 295–299

What we claim is:

1. An isolated polynucleotide encoding a polypeptide comprising the amino acid sequence of SEQ ID NO:2.

2. The polynucleotide of claim 1, comprising the nucleotide sequence as set forth in SEQ ID NO:1.

3. The polynucleotide of claim 1, encoding a polypeptide comprising amino acid residues 1–144 of SEQ ID NO: 2.

* * * * *

UNITED STATES PATENT AND TRADEMARK OFFICE
CERTIFICATE OF CORRECTION

PATENT NO. : 7,141,390 B2 Page 1 of 1
APPLICATION NO. : 10/608449
DATED : November 28, 2006
INVENTOR(S) : Zhijie Chang It is certified that error appears in the above-identified patent and that said Letters Patent is hereby corrected as shown below:

On the front page, Foreign Application Priority Data: reads "Jun. 28, 2003" should read -- Jun. 28, 2002 --.

Signed and Sealed this

Twenty-eighth Day of August, 2007

JON W. DUDAS
*Director of the United States Patent and Trademark Office*

SEQUENCE LISTING

<160> NUMBER OF SEQ ID NOS: 19

<210> SEQ ID NO 1
<211> LENGTH: 4477
<212> TYPE: DNA
<213> ORGANISM: Homo sapiens

<400> SEQUENCE: 1

```
gcggccgccg cggccaccgc ccactcgggg ctggccagcg gcgggcggcc ggggcgcaga      60
gaacggcctg gctgggcgag cgcacggcca tggcccccgtg gctgcagctc tgctccgtct     120
tctttacggt caacgcctgc ctcaacggct cgcagctggc tgtggccgct ggcgggtccg     180
gccgcgcgcg gggcgccgac acctgtggct ggaggggagt ggggccagcc agcagaaaca     240
gtgggctgta caacatcacc ttcaaatatg acaattgtac cacctacttg aatccagtgg     300
ggaagcatgt gattgctgac gcccagaata tcaccatcag ccagtatgct tgccatgacc     360
aagtggcagt caccattctt tggtccccag gggccctcgg catcgaattc ctgaaaggat     420
ttcgggtaat actggaggag ctgaagtcgg agggaagaca gtgccaacaa ctgattctaa     480
aggatccgaa gcagctcaac agtagcttca aaagaactgg aatggaatct caacctttcc     540
tgaatatgaa atttgaaacg gattatttcg taaaggttgt cccttttcct tccattaaaa     600
acgaaagcaa ttaccaccct ttcttcttta gaacccgagc ctgtgacctg ttgttacagc     660
cggacaatct agcttgtaaa cccttctgga gcctcggaa cctgaacatc agccagcatg     720
gctcggacat gcaggtgtcc ttcgaccacg caccgcacaa cttcggcttc cgtttcttct     780
atcttcacta caagctcaag cacgaaggac cttcaagcg aaagacctgt gagcaggagc     840
aaactacaga gatgaccagc tgcctccttc aaaatgtttc tccaggggat tatataattg     900
agctggtgga tgacactaac acaacaagaa aagtgatgca ttatgcctta aagccagtgc     960
actccccgtg ggccgggccc atcagagccg tggccatcac agtgccactg gtagtcatat    1020
cggcattcgc gacgctcttc actgtgatgt gccgcaagaa gcaacaagaa aatatatatt    1080
cacatttaga tgaagagagc tctgagtctt ccacatacac tgcagcactc ccaagagaga    1140
ggctccggcc gcggccgaag gtctttctct gctattccag taaagatggc cagaatcaca    1200
tgaatgtcgt ccagtgtttc gcctacttcc tccaggactt ctgtggctgt gaggtggctc    1260
tggacctgtg ggaagacttc agcctctgta gagaagggca gagagaatgg gtcatccaga    1320
agatccacga gtcccagttc atcattgtgg tttgttccaa aggtatgaag tactttgtgg    1380
acaagaagaa ctacaaacac aaaggagtg gccgaggctc ggggaaagga gagctcttcc    1440
```

-continued

```
tggtggcggt gtcagccatt gccgaaaagc tccgccaggc caagcagagt tcgtccgcgg    1500
cgctcagcaa gtttatcgcc gtctactttg attattcctg cgagggagac gtccccggta    1560
tcctagacct gagtaccaag tacagactca tggacaatct tcctcagctc tgttcccacc    1620
tgcactcccg agaccacggc ctccaggagc cggggcagca cacgcgacag ggcagcagaa    1680
ggaactactt ccggagcaag tcaggccggt ccctatacgt cgccatttgc aacatgcacc    1740
agtttattga cgaggagccc gactggttcg aaaagcagtt cgttcccttc catcctcctc    1800
cactgcgcta ccgggagcca gtcttggaga aatttgattc gggcttggtt ttaaatgatg    1860
tcatgtgcaa accagggcct gagagtgact tctgcctaaa gtagaggcg gctgttcttg      1920 gggcaaccgg accagccgac tcccagcacg agagtcagca tggggggcctg accaagacg    1980 gggaggcccg gcctgccctt gacggtagcg ccgccctgca cccctgctg cacacggtga      2040 aagccggcag ccctcggac atgccgcggg actcaggcat ctatgactcg tctgtgccct      2100
catccgagct gtctctgcca ctgatggaag gactctcgac ggaccagaca gaaacgtctt    2160
ccctgacgga gagcgtgtcc tcctcttcag gcctgggtga ggaggaacct cctgcccttc    2220
cttccaagct cctctcttct gggtcatgca aagcagatct tggttgccgc agctacactg    2280
atgaactcca cgcggtcgcc ccttttgtaac aaaacgaaag agtctaagca ttgccacttt    2340
agctgctgcc tccctctgat tccccagctc atctccctgg ttgcatggcc cacttggagc    2400
tgaggtctca tacaaggata tttggagtga atgctggcc agtacttgtt ctcccttgcc      2460
ccaacccttt accggatatc ttgacaaact ctccaatttt ctaaaatgat atggagctct    2520
gaaaggcatg tccataaggt ctgacaacag cttgccaaat ttggttagtc cttggatcag    2580
agcctgttgt gggaggtagg gaggaaatat gtaaagaaaa acaggaagat acctgcacta    2640
atcattcaga cttcattgag ctctgcaaac tttgcctgtt tgctattggc taccttgatt    2700
tgaaatgctt tgtgaaaaaa ggcactttta acatcatagc cacagaaatc aagtgccagt    2760
ctatctggaa tccatgttgt attgcagata atgttctcat ttatttttga tgtagaattt    2820
acattgccat gggtgttaaa taagctttga gtcaaaagtc aagaaagtga ctgaatatac    2880 agtcacctt tatgaaatga gtctctgtgt tactgggtgg catgactgat tgaggtgaag      2940 ctcacgggc caggctgacc gtcttgaccg ttccacttga gataggttgg tcatcgtgca      3000
gaaggcccca ggacctcagc acacacagcc tcctcttggt ctgagtaggc atcatgtggg    3060
ggccagatct gcctgctgtt tccatgggtt acatttactg tgctgtatct cagatgttgg    3120
tgtctggaag tttattctta agagactgct acccagctgg tctgtattat tggaagttgc    3180
agttcgtgct ttggttggcc ttctggtcta aagctgtgtc ctgaatatta gggatcacaa    3240
ttcactgaaa tacagcagtg tgtggaggtg atggccagtt aatctgctga actggttttg    3300
actaatgaca aacctctttt taagatggta gaatggaggt gatagtcaca aaagtaaatg    3360 ttccatttt atgaatgact ttctacagag tttctatttc taaagaaaaa acaattgttc    3420
acatcccatc tgatgattag catgtgtgta atgaatgctg tcttggtctc ccctgtggaa    3480
acccttctcc ctgtgcctta gagcaggtgt gtacatctct cactaccttt tcatgggtg      3540 ctgttagatt ttggcacccg ttttctcagc attcagccca gggaatgtgg ttttcacttc    3600
ttcgtcagat aagaccaaca tgaagggta tgttgagaaa catcctgagg caaggtggga    3660
ggtgggatgg ggcaggactt tcccttccaa gcacatgcat ggcaggtggg gaaaggggggg    3720 cttgcacccc tgctgaaaag aaaaggtttg tgtatatttc tgatgcaaat gtcatactca    3780
ctgctctgta aaggcagctg gcagcttttt gggaaaagaa cgtgctcgtc tgttctctgg    3840
```

-continued

```
catcaagttt cttgcagctg ctctgaggga gagacagtga gctgcaagac tgcctcccca    3900
taacaacagg caactcagag aagagtcatt ttatgttgtt cctatggaat ctggaatgag    3960
tgcagagctc ctacccacac atgactgccc cgccatttca tcctaggcat tctgtgaagg    4020
agattggtta gtccaaactt gctaacatac gaaaattcac ttggaacatg atgagagatt    4080
tcttattgag gccaagagat gtttcctgtc ccagaggaac cattaggagt cgcttttagg    4140
gtattcagct ttgttcatga aataaggcat ctctgagaaa gtggcccag ggagagaatg     4200 gaggactggg aggagaagca ttaactgagc tccaagggtg tgtgggcaga gagcttgcta    4260
tgtgaactca ctccttaaga aaatggaaga gaaaagaga gtgctagtta aaaaatcggg     4320
atgttttagt ttggatttag ggttttgata cttatgttga aatactaatg tttctgatca    4380
ataaaatcaa actcttaata taccgagtaa tgaaaccata gtgtgattgc ctcagaataa    4440
attgagaagt ccaaaaaaaa aaaaaaaaa aaaaaaa                              4477
```

<210> SEQ ID NO 2
<211> LENGTH: 739
<212> TYPE: PRT
<213> ORGANISM: Homo sapiens

<400> SEQUENCE: 2

```
Met Ala Pro Trp Leu Gln Leu Cys Ser Val Phe Phe Thr Val Asn Ala
1               5                   10                  15

Cys Leu Asn Gly Ser Gln Leu Ala Val Ala Ala Gly Gly Ser Gly Arg
            20                  25                  30

Ala Arg Gly Ala Asp Thr Cys Gly Trp Arg Gly Val Gly Pro Ala Ser
        35                  40                  45

Arg Asn Ser Gly Leu Tyr Asn Ile Thr Phe Lys Tyr Asp Asn Cys Thr
    50                  55                  60

Thr Tyr Leu Asn Pro Val Gly Lys His Val Ile Ala Asp Ala Gln Asn
65                  70                  75                  80

Ile Thr Ile Ser Gln Tyr Ala Cys His Asp Gln Val Ala Val Thr Ile
                85                  90                  95

Leu Trp Ser Pro Gly Ala Leu Gly Ile Glu Phe Leu Lys Gly Phe Arg
            100                 105                 110

Val Ile Leu Glu Glu Leu Lys Ser Glu Gly Arg Gln Cys Gln Gln Leu
        115                 120                 125

Ile Leu Lys Asp Pro Lys Gln Leu Asn Ser Ser Phe Lys Arg Thr Gly
    130                 135                 140

Met Glu Ser Gln Pro Phe Leu Asn Met Lys Phe Glu Thr Asp Tyr Phe
145                 150                 155                 160

Val Lys Val Val Pro Phe Pro Ser Ile Lys Asn Glu Ser Asn Tyr His
                165                 170                 175

Pro Phe Phe Phe Arg Thr Arg Ala Cys Asp Leu Leu Gln Pro Asp
            180                 185                 190

Asn Leu Ala Cys Lys Pro Phe Trp Lys Pro Arg Asn Leu Asn Ile Ser
        195                 200                 205

Gln His Gly Ser Asp Met Gln Val Ser Phe Asp His Ala Pro His Asn
    210                 215                 220

Phe Gly Phe Arg Phe Phe Tyr Leu His Tyr Lys Leu Lys His Glu Gly
225                 230                 235                 240

Pro Phe Lys Arg Lys Thr Cys Glu Gln Glu Gln Thr Thr Glu Met Thr
                245                 250                 255
```

-continued

```
Ser Cys Leu Leu Gln Asn Val Ser Pro Gly Asp Tyr Ile Ile Glu Leu
            260                 265                 270

Val Asp Asp Thr Asn Thr Thr Arg Lys Val Met His Tyr Ala Leu Lys
275             280                 285

Pro Val His Ser Pro Trp Ala Gly Pro Ile Arg Ala Val Ala Ile Thr
        290                 295                 300

Val Pro Leu Val Val Ile Ser Ala Phe Ala Thr Leu Phe Thr Val Met
305                 310                 315                 320

Cys Arg Lys Lys Gln Gln Glu Asn Ile Tyr Ser His Leu Asp Glu Glu
                325                 330                 335

Ser Ser Glu Ser Ser Thr Tyr Thr Ala Ala Leu Pro Arg Glu Arg Leu
            340                 345                 350

Arg Pro Arg Pro Lys Val Phe Leu Cys Tyr Ser Ser Lys Asp Gly Gln
        355                 360                 365

Asn His Met Asn Val Val Gln Cys Phe Ala Tyr Phe Leu Gln Asp Phe
    370                 375                 380

Cys Gly Cys Glu Val Ala Leu Asp Leu Trp Glu Asp Phe Ser Leu Cys
385                 390                 395                 400

Arg Glu Gly Gln Arg Glu Trp Val Ile Gln Lys Ile His Glu Ser Gln
                405                 410                 415

Phe Ile Ile Val Val Cys Ser Lys Gly Met Lys Tyr Phe Val Asp Lys
            420                 425                 430

Lys Asn Tyr Lys His Lys Gly Gly Arg Gly Ser Gly Lys Gly Glu
        435                 440                 445

Leu Phe Leu Val Ala Val Ser Ala Ile Ala Glu Lys Leu Arg Gln Ala
    450                 455                 460

Lys Gln Ser Ser Ala Ala Leu Ser Lys Phe Ile Ala Val Tyr Phe
465                 470                 475                 480

Asp Tyr Ser Cys Glu Gly Asp Val Pro Gly Ile Leu Asp Leu Ser Thr
                485                 490                 495

Lys Tyr Arg Leu Met Asp Asn Leu Pro Gln Leu Cys Ser His Leu His
            500                 505                 510

Ser Arg Asp His Gly Leu Gln Glu Pro Gly Gln His Thr Arg Gln Gly
        515                 520                 525

Ser Arg Arg Asn Tyr Phe Arg Ser Lys Ser Gly Arg Ser Leu Tyr Val
    530                 535                 540

Ala Ile Cys Asn Met His Gln Phe Ile Asp Glu Pro Asp Trp Phe
545                 550                 555                 560

Glu Lys Gln Phe Val Pro Phe His Pro Pro Leu Arg Tyr Arg Glu
                565                 570                 575

Pro Val Leu Glu Lys Phe Asp Ser Gly Leu Val Leu Asn Asp Val Met
            580                 585                 590

Cys Lys Pro Gly Pro Glu Ser Asp Phe Cys Leu Lys Val Glu Ala Ala
        595                 600                 605

Val Leu Gly Ala Thr Gly Pro Ala Asp Ser Gln His Glu Ser Gln His
    610                 615                 620

Gly Gly Leu Asp Gln Asp Gly Glu Ala Arg Pro Ala Leu Asp Gly Ser
625                 630                 635                 640

Ala Ala Leu Gln Pro Leu Leu His Thr Val Lys Ala Gly Ser Pro Ser
                645                 650                 655

Asp Met Pro Arg Asp Ser Gly Ile Tyr Asp Ser Ser Val Pro Ser Ser
            660                 665                 670

Glu Leu Ser Leu Pro Leu Met Glu Gly Leu Ser Thr Asp Gln Thr Glu
```

|  | 675 |  | 680 |  | 685 |  |
|---|---|---|---|---|---|---|

Thr Ser Ser Leu Thr Glu Ser Val Ser Ser Ser Gly Leu Gly Glu
    690                  695                  700

Glu Glu Pro Pro Ala Leu Pro Ser Lys Leu Leu Ser Ser Gly Ser Cys
705                710                715                720

Lys Ala Asp Leu Gly Cys Arg Ser Tyr Thr Asp Glu Leu His Ala Val
                725                730                735

Ala Pro Leu

<210> SEQ ID NO 3
<211> LENGTH: 4508
<212> TYPE: DNA
<213> ORGANISM: Homo sapiens

<400> SEQUENCE: 3

```
cagcagtggt aacgacgcac agtacgcggg ggaaaagaaa cgggaagtgg ccgtgggccg     60
gtgaattccg tgtagtggcc aagctttgtt ccaaagaggg ggaggtggtg acagtctctt    120
gcccactgaa gcgtgccaga cagagtgcta ggcatggggg cagaggtgaa tcagatgaca    180
gccacctctc accacgagga gtggctgaaa gtgtgactgg actacaggca atcctggcct    240
tgcagggag tggggccagc cagcagaaac agtgggctgt acaacatcac cttcaaatat    300
gacaattgta ccacctactt gaatccagtg gggaagcatg tgattgctga cgcccagaat    360
atcaccatca gccagtatgc ttgccatgac caagtggcag tcaccattct ttggtcccca    420
ggggccctcg gcatcgaatt cctgaaagga tttcgggtaa tactggagga gctgaagtcg    480
gaggaagac agtgccaaca actgattcta aaggatccga agcagctcaa cagtagcttc    540
aaaagaactg gaatggaatc tcaacctttc ctgaatatga aatttgaaac ggattatttc    600
gtaaaggttg tccctttcc ttccattaaa acgaaagca attaccaccc tttcttcttt    660
agaacccgag cctgtgacct gttgttacag ccggacaatc tagcttgtaa acccttctgg    720
aagcctcgga acctgaacat cagccagcat ggctcggaca tgcaggtgtc cttcgaccac    780
gcaccgcaca acttcggctt ccgtttcttc tatcttcact acaagctcaa gcacgaagga    840
cctttcaagc gaaagacctg taagcaggag caaactacag agatgaccag ctgcctcctt    900
caaaatgttt ctccagggga ttatataatt gagctggtgg atgacactaa cacaacaaga    960
aaagtgatgc attatgcctt aaagccagtg cactccccgt gggccgggcc catcagagcc   1020
gtggccatca cagtgccact ggtagtcata tcggcattcg cgacgctctt cactgtgatg   1080
tgccgcaaga agcaacaaga aaatatatat tcacatttag atgaagagag ctctgagtct   1140
tccacataca ctgcagcact cccaagagag aggctccggc cgcggccgaa ggtctttctc   1200
tgctattcca gtaaagatgg ccagaatcac atgaatgtcg tccagtgttt cgcctacttc   1260
ctccaggact tctgtggctg tgaggtggct ctggacctgt gggaagactt cagcctctgt   1320
agagaagggc agagagaatg ggtcatccag aagatccacg agtcccagtt catcattgtg   1380
gtttgttcca aaggtatgaa gtactttgtg gacaagaaga ctacaaaca caaaggaggt   1440
ggccgaggct cggggaaagg agagctcttc ctggtggcgg tgtcagccat tgccgaaaag   1500
ctccgccagg ccaagcagag ttcgtccgcg gcgctcagca gtttatcgc cgtctacttt   1560
gattattcct gcgagggaga cgtccccggt atcctagacc tgagtaccaa gtacagactc   1620
atggacaatc ttcctcagct ctgttcccac ctgcactccc gagaccacgg cctccaggag   1680
ccggggcagc acacgcgaca gggcagcaga aggaactact tccggagcaa gtcaggccgg   1740
```

-continued

```
tccctatacg tcgccatttg caacatgcac cagtttattg acgaggagcc cgactggttc      1800
gaaaagcagt tcgttcccett ccatcctcct ccactgcgct accgggagcc agtcttggag     1860
aaatttgatt cgggcttggt tttaaatgat gtcatgtgca aaccagggcc tgagagtgac     1920
ttctgcctaa aggtagaggc ggctgttctt ggggcaaccg gaccagccga ctcccagcac     1980
gagagtcagc atgggggcct ggaccaagac ggggaggccc ggcctgccct tgacggtagc     2040
gccgccctgc aaccectgct gcacacggtg aaagccggca gccctcgga catgccgcgg     2100 gactcaggca tctatgactc gtctgtgccc tcatccgagc tgtctctgcc actgatggaa     2160
ggactctcga cggaccagac agaaacgtct ccctgacgg agagcgtgtc ctcctcttca     2220
ggcctgggtg aggaggaacc tcctgccctt ccttccaagc tcctctcttc tgggtcatgc     2280
aaagcagatc ttggttgccg cagctacact gatgaactcc acgcggtcgc cccttttgtaa  2340 caaaacgaaa gagtctaagc attgccactt tagctgctgc ctccctctga ttccccagct    2400
catctccctg gttgcatggc ccacttggag ctgaggtctc atacaaggat atttggagtg    2460
aaatgctggc cagtacttgt tctcccttgc cccaacccett taccggatat cttgacaaac   2520
tctccaattt tctaaaatga tatggagctc tgaaaggcat gtccataagg tctgacaaca    2580
gcttgccaaa tttggttagt ccttggatca gagcctgttg tgggaggtag ggaggaaata    2640
tgtaaagaaa aacaggaaga tacctgcact aatcattcag acttcattga gctctgcaaa    2700 cttgcctgt ttgctattgg ctaccttgat ttgaaatgct ttgtgaaaaa aggcactttt    2760
aacatcatag ccacagaaat caagtgccag tctatctgga atccatgttg tattgcagat    2820
aatgttctca tttattttg atgtagaatt tacattgcca tgggtgttaa ataagctttg   2880
agtcaaaagt caagaaagtg actgaatata cagtcacctt ttatgaaatg agtctctgtg   2940
ttactgggtg gcatgactga ttgaggtgaa gctcacgggg ccaggctgac cgtcttgacc    3000
gttccacttg agataggttg gtcatcgtgc agaaggcccc aggacctcag cacacacagc    3060
ctcctcttgg tctgagtagg catcatgtgg gggccagatc tgcctgctgt tccatgggt    3120 tacatttact gtgctgtatc tcagatgttg gtgtctggaa gtttattctt aagagactgc    3180
tacccagctg gtctgtatta ttggaagttg cagttcgtgc tttggttggc cttctggtct    3240
aaagctgtgt cctgaatatt agggatcaca attcactgaa atacagcagt gtgtggaggt   3300
gatggccagt taatctgctg aactggtttt gactaatgac aaacctcttt ttaagatggt   3360
agaatggagg tgatagtcac aaaagtaaat gttccatttt tatgaatgac tttctacaga   3420
gtttctattt ctaaagaaaa aacaattgtt cacatcccat ctgatgatta gcatgtgtgt   3480
aatgaatgct gtcttggtct cccctgtgga aacccttctc cctgtgcctt agagcaggtg   3540
tgtacatctc tcactaccett tctcatgggt gctgttagat ttttggcaccc gttttctcag  3600 cattcagccc agggaatgtg gttttcactt cttcgtcaga taagaccaac atgaagggt    3660 atgttgagaa acatcctgag gcaaggtggg aggtgggatg gggcaggact ttcccttcca    3720
agcacatgca tggcaggtgg ggaaggggg gcttgcaccc ctgctggaaa gaaaaggttt    3780
gtgtatattt ctgatgcaaa tgtcatactc actgctctgt aaaggcagct ggcagctttt   3840
tgggaaaaga acgtgctcgt ctgttctctg gcatcaagtt tcttgcagct gctctgaggg    3900
agagacagtg agctgcaaga ctgcctcccc ataacaacag gcaactcaga gaagagtcat    3960
tttatgttgt tccatatggaa tctggaatga gtgcagagct cctacccaca catgactgcc    4020
ccgccatttc atcctaggca ttctgtgaag gagattggtt agtccaaact tgctaacata    4080
cgaaaattca cttggaacat gatgagagat ttcttattga ggccaagaga tgtttcctgt    4140
```

-continued

```
cccagaggaa ccattaggag tcgcttttag ggtattcagc tttgttcatg aaataaggca   4200
tctctgagaa agtggcccca gggagagaat ggaggactgg gaggagaagc attaactgag   4260
ctccaagggt gtgtgggcag agagcttgct atgtgaactc actccttaag aaaatggaag   4320
agaaaaagag agtgctagtt aaaaaatcgg gatgttttag tttggattta gggttttgat   4380
acttatgttg aaatactaat gtttctgatc aataaaatca aactcttaat ataccgagta   4440
atgaaaccat agtgtgattg cctcagaata aattgagaag tccaaaaaaa aaaaaaaaaa   4500
aaaaaaaa                                                            4508
```

<210> SEQ ID NO 4
<211> LENGTH: 595
<212> TYPE: PRT
<213> ORGANISM: Homo sapiens

<400> SEQUENCE: 4

```
Met Glu Ser Gln Pro Phe Leu Asn Met Lys Phe Glu Thr Asp Tyr Phe
1               5                   10                  15

Val Lys Val Val Pro Phe Pro Ser Ile Lys Asn Glu Ser Asn Tyr His
                20                  25                  30

Pro Phe Phe Phe Arg Thr Arg Ala Cys Asp Leu Leu Leu Gln Pro Asp
            35                  40                  45

Asn Leu Ala Cys Lys Pro Phe Trp Lys Pro Arg Asn Leu Asn Ile Ser
    50                  55                  60

Gln His Gly Ser Asp Met Gln Val Ser Phe Asp His Ala Pro His Asn
65                  70                  75                  80

Phe Gly Phe Arg Phe Phe Tyr Leu His Tyr Lys Leu Lys His Glu Gly
                85                  90                  95

Pro Phe Lys Arg Lys Thr Cys Lys Gln Glu Gln Thr Thr Glu Met Thr
            100                 105                 110

Ser Cys Leu Leu Gln Asn Val Ser Pro Gly Asp Tyr Ile Ile Glu Leu
        115                 120                 125

Val Asp Asp Thr Asn Thr Thr Arg Lys Val Met His Tyr Ala Leu Lys
    130                 135                 140

Pro Val His Ser Pro Trp Ala Gly Pro Ile Arg Ala Val Ala Ile Thr
145                 150                 155                 160

Val Pro Leu Val Val Ile Ser Ala Phe Ala Thr Leu Phe Thr Val Met
                165                 170                 175

Cys Arg Lys Lys Gln Gln Glu Asn Ile Tyr Ser His Leu Asp Glu Glu
            180                 185                 190

Ser Ser Glu Ser Ser Thr Tyr Thr Ala Ala Leu Pro Arg Glu Arg Leu
        195                 200                 205

Arg Pro Arg Pro Lys Val Phe Leu Cys Tyr Ser Ser Lys Asp Gly Gln
    210                 215                 220

Asn His Met Asn Val Val Gln Cys Phe Ala Tyr Phe Leu Gln Asp Phe
225                 230                 235                 240

Cys Gly Cys Glu Val Ala Leu Asp Leu Trp Glu Asp Phe Ser Leu Cys
                245                 250                 255

Arg Glu Gly Gln Arg Glu Trp Val Ile Gln Lys Ile His Glu Ser Gln
            260                 265                 270

Phe Ile Ile Val Val Cys Ser Lys Gly Met Lys Tyr Phe Val Asp Lys
        275                 280                 285

Lys Asn Tyr Lys His Lys Gly Gly Gly Arg Gly Ser Gly Lys Gly Glu
    290                 295                 300
```

Leu Phe Leu Val Ala Val Ser Ala Ile Ala Glu Lys Leu Arg Gln Ala
305                 310                 315                 320

Lys Gln Ser Ser Ala Ala Leu Ser Lys Phe Ile Ala Val Tyr Phe
            325                 330                 335

Asp Tyr Ser Cys Glu Gly Asp Val Pro Gly Ile Leu Asp Leu Ser Thr
            340                 345                 350

Lys Tyr Arg Leu Met Asp Asn Leu Pro Gln Leu Cys Ser His Leu His
            355                 360                 365

Ser Arg Asp His Gly Leu Gln Glu Pro Gly Gln His Thr Arg Gln Gly
370                 375                 380

Ser Arg Arg Asn Tyr Phe Arg Ser Lys Ser Gly Arg Ser Leu Tyr Val
385                 390                 395                 400

Ala Ile Cys Asn Met His Gln Phe Ile Asp Glu Pro Asp Trp Phe
            405                 410                 415

Glu Lys Gln Phe Val Pro Phe His Pro Pro Leu Arg Tyr Arg Glu
            420                 425                 430

Pro Val Leu Glu Lys Phe Asp Ser Gly Leu Val Leu Asn Asp Val Met
            435                 440                 445

Cys Lys Pro Gly Pro Glu Ser Asp Phe Cys Leu Lys Val Glu Ala Ala
450                 455                 460

Val Leu Gly Ala Thr Gly Pro Ala Asp Ser Gln His Glu Ser Gln His
465                 470                 475                 480

Gly Gly Leu Asp Gln Asp Gly Glu Ala Arg Pro Ala Leu Asp Gly Ser
            485                 490                 495

Ala Ala Leu Gln Pro Leu Leu His Thr Val Lys Ala Gly Ser Pro Ser
            500                 505                 510

Asp Met Pro Arg Asp Ser Gly Ile Tyr Asp Ser Ser Val Pro Ser Ser
            515                 520                 525

Glu Leu Ser Leu Pro Leu Met Glu Gly Leu Ser Thr Asp Gln Thr Glu
530                 535                 540

Thr Ser Ser Leu Thr Glu Ser Val Ser Ser Ser Gly Leu Gly Glu
545                 550                 555                 560

Glu Glu Pro Pro Ala Leu Pro Ser Lys Leu Leu Ser Ser Gly Ser Cys
            565                 570                 575

Lys Ala Asp Leu Gly Cys Arg Ser Tyr Thr Asp Glu Leu His Ala Val
            580                 585                 590

Ala Pro Leu
      595

<210> SEQ ID NO 5
<211> LENGTH: 32
<212> TYPE: DNA
<213> ORGANISM: Artificial
<220> FEATURE:
<223> OTHER INFORMATION: Primer

<400> SEQUENCE: 5
tatagcgata tcatggacaa actcagggtg cc                                    32

<210> SEQ ID NO 6
<211> LENGTH: 30
<212> TYPE: DNA
<213> ORGANISM: Artificial
<220> FEATURE:
<223> OTHER INFORMATION: Primer

<400> SEQUENCE: 6
aatgaattcc taggagcagg ccacatagcc                    30

<210> SEQ ID NO 7
<211> LENGTH: 25
<212> TYPE: DNA
<213> ORGANISM: Artificial
<220> FEATURE:
<223> OTHER INFORMATION: Primer

<400> SEQUENCE: 7
ataaagctta tggccccgtg gctgc                         25

<210> SEQ ID NO 8
<211> LENGTH: 26
<212> TYPE: DNA
<213> ORGANISM: Artificial
<220> FEATURE:
<223> OTHER INFORMATION: Primer

<400> SEQUENCE: 8
ttctcgagtt acaaaggggc gaccgc                        26

<210> SEQ ID NO 9
<211> LENGTH: 32
<212> TYPE: DNA
<213> ORGANISM: Artificial
<220> FEATURE:
<223> OTHER INFORMATION: Primer

<400> SEQUENCE: 9
tatagcgata tcatggacaa actcagggtg cc                 32

<210> SEQ ID NO 10
<211> LENGTH: 29
<212> TYPE: DNA
<213> ORGANISM: Artificial
<220> FEATURE:
<223> OTHER INFORMATION: Primer

<400> SEQUENCE: 10
tatagaattc cagcagggcc agaaccgtc                     29

<210> SEQ ID NO 11
<211> LENGTH: 25
<212> TYPE: DNA
<213> ORGANISM: Artificial
<220> FEATURE:
<223> OTHER INFORMATION: Primer

<400> SEQUENCE: 11
attgaattct gccgcaagaa gcaac                         25

<210> SEQ ID NO 12
<211> LENGTH: 27
<212> TYPE: DNA
<213> ORGANISM: Artificial
<220> FEATURE:
<223> OTHER INFORMATION: Primer

<400> SEQUENCE: 12
attggatcct tacaaagggg cgaccgc                       27

<210> SEQ ID NO 13
<211> LENGTH: 30
<212> TYPE: DNA

```
<213> ORGANISM: Artificial
<220> FEATURE:
<223> OTHER INFORMATION: Primer

<400> SEQUENCE: 13
ataggtacca tggaatctca acctttcctg                                              30

<210> SEQ ID NO 14
<211> LENGTH: 25
<212> TYPE: DNA
<213> ORGANISM: Artificial
<220> FEATURE:
<223> OTHER INFORMATION: Primer

<400> SEQUENCE: 14
ataggatccc aaagggcga ccgcg                                                    25

<210> SEQ ID NO 15
<211> LENGTH: 31
<212> TYPE: DNA
<213> ORGANISM: Artificial
<220> FEATURE:
<223> OTHER INFORMATION: Primer

<400> SEQUENCE: 15
cgtggtaccg atggaatctc aacctttcct g                                            31

<210> SEQ ID NO 16
<211> LENGTH: 24
<212> TYPE: DNA
<213> ORGANISM: Artificial
<220> FEATURE:
<223> OTHER INFORMATION: Primer

<400> SEQUENCE: 16
atatctagag ggcccggccc acgg                                                    24

<210> SEQ ID NO 17
<211> LENGTH: 23
<212> TYPE: DNA
<213> ORGANISM: Artificial
<220> FEATURE:
<223> OTHER INFORMATION: Primer

<400> SEQUENCE: 17
agctcaccat ggatgatgat atc                                                     23

<210> SEQ ID NO 18
<211> LENGTH: 24
<212> TYPE: DNA
<213> ORGANISM: Artificial
<220> FEATURE:
<223> OTHER INFORMATION: Primer

<400> SEQUENCE: 18
tgttgaaggt ctcaaacatg atct                                                    24

<210> SEQ ID NO 19
<211> LENGTH: 16
<212> TYPE: DNA
<213> ORGANISM: Artificial
```

-continued

```
<220> FEATURE:
<223> OTHER INFORMATION: Primer

<400> SEQUENCE: 19
agatttctag gaattc                                               16
```